(12) United States Patent
Dong et al.

(10) Patent No.: US 6,509,336 B1
(45) Date of Patent: Jan. 21, 2003

(54) IMIDAZOLYL DERIVATIVES

(75) Inventors: Zheng Xin Dong, Framingham, MA (US); Yeelana Shen, Franklin, MA (US)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 10/151,265

(22) Filed: May 20, 2002

Related U.S. Application Data

(62) Division of application No. 09/719,720, filed on May 22, 2001, now Pat. No. 6,420,555, which is a continuation of application No. 09/098,141, filed on Jun. 16, 1998.
(60) Provisional application No. 60/089,483, filed on Jun. 16, 1998.

(51) Int. Cl.[7] ............... C07D 413/14; A61K 31/415
(52) U.S. Cl. ............... 514/235.8; 514/254.05; 514/339; 514/397
(58) Field of Search ............... 514/235.8, 397, 514/254.05, 339

(56) References Cited

U.S. PATENT DOCUMENTS

| 5,968,952 A | 10/1999 | Venet et al. |
| 6,037,350 A | 3/2000 | Venet et al. |

FOREIGN PATENT DOCUMENTS

| EP | 0 371 559 A | 6/1990 |
| WO | 93 25548 A | 12/1993 |
| WO | 96 20200 A | 7/1996 |
| WO | 96 39137 A | 12/1996 |
| WO | 97 16443 A | 5/1997 |
| WO | 97 21701 A | 6/1997 |
| WO | 97 36901 a | 10/1997 |
| WO | 98 40383 A | 9/1998 |
| WO | WO 00/02558 | 1/2000 |

*Primary Examiner*—Joseph K. McKane
*Assistant Examiner*—Kamal Saeed
(74) *Attorney, Agent, or Firm*—Fish & Richardson; Brian R. Morrill; Alan F. Feeney

(57) ABSTRACT

The present invention is directed to imidazolyl derivatives of formula (II), wherein the variables are defined in the specification, which are useful as prenyl transferase inhibitors.

2 Claims, No Drawings

IMIDAZOLYL DERIVATIVES

CROSS REFERENCE TO RELATED APPLICATIONS

This application claims priority benefit of and is a divisional application of U.S. application Ser. No. 09/719,720, filed May 22, 2001 now U.S. Pat. No. 6,420,555, which is a con't of U.S. application Ser. No. 09/098,141, filed Jun. 16, 1998, which claims benefits of U.S. application Serial No. 60/089,483, filed Jun. 16, 1998, all of which are incorporated by reference in their entirety.

BACKGROUND OF THE INVENTION

The present invention is directed to imidazolyl derivatives which are useful as prenyl transferase inhibitors.

The Ras family of proteins are important in the signal transduction pathway modulating cell growth. The protein is produced in the ribosome, released into the cytosol, and post-translationally modified. The first step in the series of post-translational modifications is the alkylation of $Cys^{168}$ with farnesyl or geranylgeranyl pyrophosphate in a reaction catalyzed by prenyl transferase enzymes such as farnesyl transferase and geranylgeranyl transferase (Hancock, J F, et al., Cell 57:1167–1177 (1989)). Subsequently, the three C-terminal amino acids are cleaved (Gutierrez, L., et al., EMBO J. 8:1093–1098 (1989)), and the terminal Cys is converted to a methyl ester (Clark, S., et al., Proc. Nat'l Acad. Sci. (USA) 85:4643–647 (1988)). Some forms of Ras are also reversibly palmitoylated on cysteine residues immediately N-terminal to $Cys^{168}$ (Buss, J E et al., Mol. Cell. Biol. 6:116–122 (1986)). It is believed that these modifications increase the hydrophobicity of the C-terminal region of Ras, causing it to localize at the surface of the cell membrane. Localization of Ras to the cell membrane is necessary for signal transduction (Willumsen, B M, et al., Science 310:583–586 (1984)).

Oncogenic forms of Ras are observed in a relatively large number of cancers including over 50 percent of colon cancers and over 90 percent of pancreatic cancers (Bos, J L, Cancer Research 49:4682–4689 (1989)). These observations suggest that intervention in the function of Ras mediated signal transduction may be useful in the treatment of cancer.

Previously, it has been shown that the C-terminal tetrapeptide of Ras is a "CAAX" motif (wherein C is cysteine, A is an aliphatic amino acid, and X is any amino acid). Tetrapeptides having this structure have been shown to be inhibitors of prenyl transferases (Reiss, et al., Cell 62:81–88 (1990)). Poor potency of these early farnesyl transferase inhibitors has prompted the search for new inhibitors with more favorable pharmacokinetic behavior (James, G L, et al., Science 260:1937–1942 (1993); Kohl, N E, et al., Proc. Nat'l Acad. Sci. USA 91:9141–9145 (1994); deSolms, SJ, et al., J. Med. Chem. 38:3967–3971 (1995); Nagasu, T, et al., Cancer Research 55:5310–5314 (1995); Lerner, E C, et al., J. Biol. Chem. 270:26802–26806 (1995); Lerner, E C, et al., J. Biol. Chem. 270:26770 (1995); and James, et al., Proc. Natl. Acad. Sci. USA 93:4454 (1996)).

Recently, it has been shown that a prenyl transferase inhibitor can block growth of Ras-dependent tumors in nude mice (Kohl, N. E., et al., Proc. Nat'l Acad. Sci. USA 91:9141–9145 (1994)). In addition, it has been shown that over 70 percent of a large sampling of tumor cell lines are inhibited by prenyl transferase inhibitors with selectivity over non-transformed epithelial cells (Sepp-Lorenzino, I., et al., Cancer Research, 55:5302–5309 (1995)).

SUMMARY OF THE INVENTION

In one aspect, this invention provides a compound of formula (I),

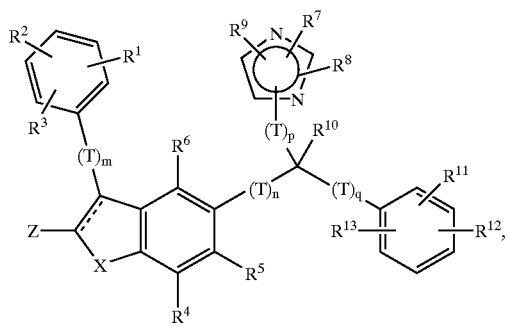

(I)

or a pharmaceutically acceptable salt thereof,
wherein
——————represents an optional bond;
m, n, p, and q are each independently 0 or 1;
T for each occurrence is independently selected from the group consisting of $CR^{26}R^{27}$, S, O, C(O), $S(O)_2$ and $NR^{28}$;
X is N—Y, O or S where Y is selected from the group consisting of H, $CR^{14}R^{15}R^{16}$, $S(O)R^{17}$, $S(O)_2R^{18}$, $C(O)R^{19}$, $C(O)NR^{20}R^{21}$, $C(S)NR^{22}R^{23}$, $C(O)OR^{24}$, $C(S)OR^{25}$, $S(O)NR^{29}R^{30}$ and $S(O)_2NR^{31}R^{32}$;
Z is selected from the group consisting of H, cyano, halo, $CR^{14}R^{15}R^{16}$, $S(O)R^{17}$, $S(O)_2R^{18}$ and $C(O)R^{19}$;
$R^1$, $R^2$, $R^3$, $R^4$, $R^5$, $R^6$, $R^{11}$, $R^{12}$, $R^{13}$, $R^{14}$, $R^{15}$, $R^{16}$, $R^{26}$ and $R^{27}$ are each independently selected from the group consisting of H, halo, hydroxy, thio and cyano, or an optionally substituted moiety selected from the group consisting of alkyl, alkenyl, alkynyl, cycloalkyl, cycloalkyl-alkyl, aryl, arylalkyl, alkyloxy, aryloxy, alkylthio, arylthio, alkylamino, arylamino and alkyl carbonyl amino;
or $R^1$ and $R^2$ when on adjacent positions, or $R^4$ and $R^5$, or $R^{11}$ and $R^{12}$, are taken together to form a bivalent radical selected from the group consisting of —O—CH$_2$—O—, —O—CH$_2$—CH$_2$—O—, —O—CH═CH—, —O—CH$_2$—CH$_2$—, —O—CH$_2$—CH$_2$—CH$_2$— and —CR$^{33}$═CR$^{34}$—CR$^{35}$═CR$^{36}$—; $R^7$, $R^8$ and $R^9$ are each independently selected from the group consisting of H, halo, aryl, alkyl, substituted alkyl, alkyloxy, alkylthio, aryloxy, arylthio amino, mono- or di-alkylamino, hydroxycarbonyl, alkoxycarbonyl, alkyl-S(O)-alkyl, alkyl-S(O)$_2$-alkyl, cyanoarylalkyl, arylalkyl and substituted arylalkyl;
$R^{10}$ is selected from the group consisting of H, amino, azido, hydroxy, halo, alkyl, substituted alkyl, cyano, hydroxyalkyl, hydroxycarbonyl, aminoalkyl, mono- or di-alkylaminoalkyl, mono- or di-alkylamino, alkoxy, alkylcarbonylalkyl, cyanoalkyl, alkyloxycarbonylalkyl, carboxyalkyl, cycloalkyl, cycloalkylamino, cycloalkylhydroxy, imidazoyl, substituted imidazoyl, aminocarbonylalkyl, aryloxy, thio, alkylthio, $OS(O_2)R^{18}$, $OC(O)R^{19}$, $OC(O)NR^{20}R^{21}$, $OC(S)NR^{22}R^{23}$, $OS(O)NR^{29}R^{30}$, $OS(O)_2NR^{31}R^{32}$ and arylthio; and $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, $R^{31}$, $R^{32}$ and $R^{37}$ for each occurrence are each independently selected from the group consisting of H, alkyl, substituted alkyl, alkenyl, cycloalkyl, aryl and arylalkyl;
or $R^{20}$ and $R^{21}$, or $R^{22}$ and $R^{23}$, or $R^{29}$ and $R^{30}$, or $R^{31}$ and $R^{32}$ are taken together to form a bivalent radical selected from the group consisting of —(CH$_2$)$_r$—NR$^{37}$—(CH$_2$)$_s$—, —(CH$_2$)$_r$—O—(CH$_2$)$_s$— and —(CR$^{38}$R$^{39}$)$_t$—, where r and s are each independently 1 to 3 and t is 2 to 6;

R$^{33}$, R$^{34}$, R$^{35}$, R$^{36}$, R$^{38}$ and R$^{39}$ are each independently selected from the group consisting of H, halo, cyano, alkyl, substituted alkyl, aryl, substituted aryl, alkyloxy, aryloxy, alkylthio, arylthio, alkylamino, arylamino, hydroxy and thio.

A preferred group of compounds of the immediately foregoing compounds is where m, n, p and q are each 0.

A preferred group of compounds of the immediately foregoing compounds is where R$^1$, R$^2$, R$^3$, R$^4$, R$^5$, R$^6$, R$^{11}$, R$^{12}$ and R$^{13}$ are each H, halo, alkyl, substituted alkyl, cyano or alkyloxy.

A preferred group of compounds of the immediately foregoing compounds is where R$^{10}$ is OH, H, halo, azido, amino, mono- or di-alkylamino, OS(O$_2$)R$^{18}$, OC(O)NR$^{20}$R$^{21}$ or OS(O)$_2$NR$^{31}$R$^{32}$.

A preferred group of compounds of the immediately foregoing compounds is where R$^7$, R$^8$ and R$^9$ are each H, alkyl, substituted alkyl, amino or cyanoarylalkyl.

A preferred group of compounds of the immediately foregoing compounds is where X is N—Y and Y is H, CR$^{14}$R$^{15}$R$^{16}$, S(O)$_2$R$^{18}$, C(O)NR$^{20}$R$^{21}$ or S(O)$_2$NR$^{29}$R$^{30}$.

A preferred group of compounds of the immediately foregoing compounds is where R$^1$, R$^2$, R$^3$, R$^{11}$, R$^{12}$ and R$^{13}$ are each halo or hydrogen.

A preferred group of compounds of the immediately foregoing compounds is where R$^1$, R$^2$, R$^3$, R$^{11}$, R$^{12}$ and R$^{13}$ are each chloro or hydrogen.

A preferred group of compounds of the immediately foregoing compounds is where R$^7$, R$^8$, and R$^9$ are each (C$_1$–C$_4$)alkyl or hydrogen.

A preferred group of compounds of the immediately foregoing compounds is where R$^7$, R$^8$, and R$^9$ are each methyl or hydrogen.

A preferred group of compounds of the immediately foregoing compounds is where R$^{10}$ is OH, amino, OS(O$_2$)R$^{18}$, or OC(O)NR$^{20}$R$^{21}$.

A preferred group of compounds of the immediately foregoing compounds is where R$^4$, R$^5$ and R$^6$ are each H.

A preferred group of compounds of the immediately foregoing compounds is where Z is hydrogen.

A preferred group of compounds of the immediately foregoing compounds is where Y is H, methyl, S(O)$_2$R$^{18}$, C(O)NR$^{20}$R$^{21}$ or S(O)$_2$R$^{29}$R$^{30}$.

A preferred group of compounds of the immediately foregoing compounds is where said compounds are of the formula:

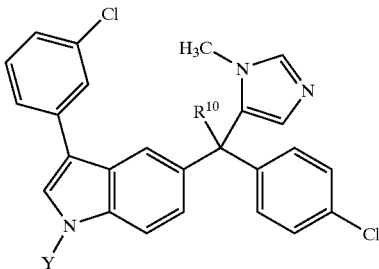

wherein
R$^{10}$ is OH and Y is H;
R$^{10}$ is NH$_2$ and Y is —S(O)$_2$—CH$_3$;
R$^{10}$ is OH and Y is —S(O)$_2$—CH$_3$;
R$^{10}$ is OH and Y is —C(O)—N(CH$_3$)$_2$;
R$^{10}$ is NH$_2$ and Y is —C(O)—N(CH$_3$)$_2$;
R$^{10}$ is NH$_2$ and Y is H;
R$^{10}$ is OH and Y is

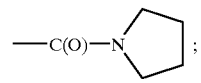

R$^{10}$ is NH$_2$ and Y is

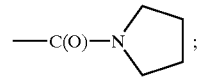

R$^{10}$ is OH and Y is —S(O)$_2$-Phenyl;
R$^{10}$ is NH$_2$ and Y is —S((O)$_2$-Phenyl;
R$^{10}$ is OH and Y is —C(O)—N(CH$_2$CH$_3$)$_2$;
R$^{10}$ is NH$_2$ and Y is —C(O)—N(CH$_2$CH$_3$)$_2$;
R$^{10}$ is OH and Y is —CH$_3$; and
R$^{10}$ is NH$_2$ and Y is —CH$_3$.

A preferred group of compounds of the immediately foregoing compounds is where said compounds are of the formula

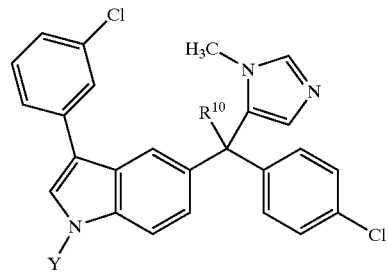

wherein
R$^{10}$ is OH and Y is H;
R$^{10}$ is NH$_2$ and Y is —S(O)$_2$—CH$_3$;
R$^{10}$ is OH and Y is —S(O)$_2$—CH$_3$;
R$^{10}$ is NH$_2$ and Y is —S(O)$_2$—CH$_3$; and
R$^{10}$ is OH and Y is —C(O)—N(CH$_3$)$_2$.

A preferred group of compounds of the immediately foregoing compounds is where said compounds are of the formula

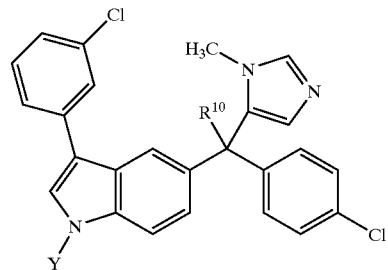

wherein
R$^{10}$ is OH and Y is H; and
R$^{10}$ is OH and —S(O)$_2$—CH$_3$.

In another aspect, this invention provides a compound of formula (II),

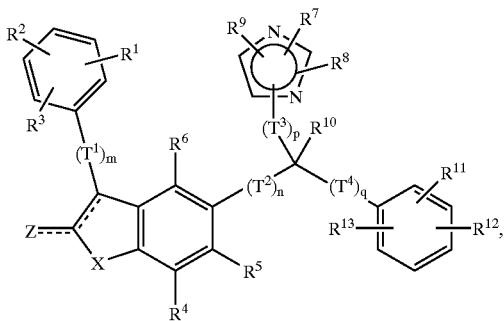

(II)

or a pharmaceutically acceptable salt thereof,
wherein

——————— represents an optional bond, provided that only one of the optional bonds is present in a compound of formula (I);

m, n, p, and q are each independently 0, 1 or 2;

$T^1$, $T^2$, $T^3$ and $T^4$ for each occurrence are each independently selected from the group consisting of $CR^{26}R^{27}$, S, O, C(O), $S(O)_2$ and $NR^{28}$;

X is N—Y, O or S where Y is selected from the group consisting of H, $CR^{14}R^{15}R^{16}$, $S(O)R^{17}$, $S(O)_2R^{18}$, $C(O)R^{19}$, $C(O)NR^{20}R^{21}$, $C(S)NR^{22}R^{23}$, $C(O)OR^{24}$, $C(S)OR^{25}$, $S(O)NR^{29}R^{30}$ and $S(O)_2NR^{31}R^{32}$;

Z is selected from the group consisting of H, hydroxy, alkoxy, aryloxy, cyano, halo, $C^{14}R^{15}R^{16}$, $S(O)R^{17}$, $S(O)_2R^{18}$, $C(O)R^{19}$, $C(O)NR^{20}R^{21}$, $C(O)OR^{24}$, $C(S)NR^{22}R^{23}$, $C(S)OR^{25}$, $S(O)NR^{29}R^{30}$ and $S(O)_2NR^{31}R^{32}$, provided that when the optional bond connected to Z is present then Z is oxygen or sulfur;

$R^1$, $R^2$, $R^3$, $R^4$, $R^5$, $R^6$, $R^{11}$, $R^{12}$, $R^{13}$, $R^{14}$, $R^{15}$, $R^{16}$, $R^{26}$ and $R^{27}$ for each each independently selected from the group consisting of H, halo, hydroxy, thio and cyano, or an optionally substituted moiety selected from the group consisting of alkyl, alkenyl, alkynyl, cycloalkyl, cycloalkyl-alkyl, aryl, arylalkyl, alkyloxy, aryloxy, alkylthio, arylthio, alkylamino, arylamino and alkyl carbonyl amino;

or each pair of $R^1$ and $R^2$, $R^4$ and $R^5$, and $R^{11}$ and $R^{12}$ when on adjacent positions, is independently taken together to form a bivalent radical selected from the group consisting of —O—CH$_2$—O—, —O—CH$_2$—CH$_2$—O—, —O—CH=CH—, —O—CH$_2$—CH$_2$—, —O—CH$_2$—CH$_2$—CH$_2$— and —CR$^{33}$=CR$^{34}$—CR$^{35}$=CR$^{36}$—;

$R^7$, $R^8$ and $R^9$ are each independently H, halo, amino, cyano, hydroxycarbonyl, or an optionally substituted moiety selected from the group consisting of aryl, alkyl, alkyloxy, alkylthio, aryloxy, arylthio, alkoxycarbonyl, alkyl-S(O)-alkyl, alkyl-S(O)$_2$-alkyl, cyanoarylalkyl and arylalkyl, provided that when $R^7$, $R^8$ or $R^9$ is bound to one of the nitrogen atoms of the imidazolyl ring, $R^7$, $R^8$ or $R^9$ is H or an optionally substituted moiety selected from the group consisting of aryl, alkyl, alkoxycarbonyl, alkyl-S(O)-alkyl, alkyl-S(O)$_2$-alkyl, cyanoarylalkyl and arylalkyl;

$R^{10}$ is selected from the group consisting of H, amino, azido, hydroxy, halo, alkyl, substituted alkyl, cyano, hydroxycarbonyl, mono- or di-alkylamino, alkyloxy, cycloalkyl, cycloalkylamino, cycloalkyloxy, imidazolyl, substituted imidazolyl, aryloxy, thio, alkylthio, arylthio, $OS(O)_2R^{18}$, $OC(O)R^{19}$, $OC(O)NR^{20}R^{21}$, $OC(S)NR^{22}R^{23}$, $OS(O)NR^{29}R^{30}$ and $OS(O)_2NR^{31}R^{32}$;

$R^{17}$ and $R^{18}$, for each occurrence are each independently H, OH or an optionally substituted moiety selected from the group consisting of alkyl, alkenyl, cycloalkyl, aryl, arylalkyl and heterocyclyl;

$R^{19}$, $R^{20}$, $R^{21}$, $R^{22}$, $R^{23}$, $R^{24}$, $R^{25}$, $R^{28}$, $R^{29}$, $R^{30}$, $R^{31}$ and $R^{32}$ for each occurrence a independently H or an optionally substituted moiety selected from the group consisting of alkyl, alkenyl, cycloalkyl, aryl, arylalkyl and heterocyclyl;

or each pair of $R^{20}$ and $R^{21}$, $R^{22}$ and $R^{23}$, $R^{29}$ and $R^{30}$, and $R^{31}$ and $R^{32}$ is independently taken together to form a bivalent radical selected from the group consisting of —(CH$_2$)$_r$—NR$^{40}$—(CH$_2$)$_s$—, —(CH$_2$)$_r$—O—(CH$_2$)$_s$—, —(CR$^{38}$R$^{39}$)$_t$— and —(CH$_2$)$_r$—NR$^{40}$—(C(O))$_u$—, where r and s are each independently 1 to 3, t is 2 to 6 and u is 1 or 2;

$R^{33}$, $R^{34}$, $R^{35}$, $R^{36}$, $R^{38}$ and $R^{39}$ for each occurrence are each independently selected from the group consisting of H, amino, halo, cyano, alkyl, substituted alkyl, aryl, substituted aryl, alkyloxy, aryloxy, alkylthio, arylthio, mono- or di-alkylamino, arylamino, hydroxy, heterocyclyl and thio;

and $R^{40}$ is H, $S(O)_2R^{18}$, $C(O)R^{19}$, $C(O)NR^{20}R^{21}$, $C(S)NR^{22}R^{23}$, $C(O)OR^{24}$, $C(S)OR^{25}$, $S(O)_2NR^{31}R^{32}$ or an optionally substituted moiety selected from the group consisting of alkyl, alkenyl, cycloalkyl, aryl, arylalkyl and heterocyclyl.

A preferred group of compounds of the immediately foregoing compounds is where m, n, p and q are each 0.

A preferred group of compounds of the immediately foregoing compounds is where $R^1$, $R^2$, $R^3$, $R^4$, $R^5$, $R^6$, $R^{11}$, $R^{12}$ and $R^{13}$ are each H, halo, alkyl, substituted alkyl, cyano or alkyloxy.

A preferred group of compounds of the immediately foregoing compounds is where $R^{10}$ is OH, H, halo, azido, amino, mono- or di-alkylamino, $OS(O)_2R^{18}$, $OC(O)NR^{20}R^{21}$ or $OS(O)_2NR^{31}R^{32}$.

A preferred group of compounds of the immediately foregoing compounds is where $R^7$, $R^8$ and $R^9$ are each H, alkyl, substituted alkyl or cyanoarylalkyl.

A preferred group of compounds of the immediately foregoing compounds is where X is N—Y and Y is H, $CR^{14}R^{15}R^{16}$, $S(O)_2R^{18}$, $C(O)R^{19}$, $C(O)NR^{20}R^{21}$, $C(O)OR^{24}$ or $S(O)_2NR^{31}R^{32}$.

A preferred group of compounds of the immediately foregoing compounds is where $R^1$, $R^2$, $R^3$, $R^{11}$, $R^{12}$ and $R^{13}$ are each halo or H.

A preferred group of compounds of the immediately foregoing compounds is where $R^1$, $R^2$, $R^3$, $R^{11}$, $R^{12}$ and $R^{13}$ are each chloro or H.

A preferred group of compounds of the immediately foregoing compounds is where $R^7$, $R^8$, and $R^9$ are each (C$_1$–C$_4$)alkyl or H.

A preferred group of compounds of the immediately foregoing compounds is where $R^7$, $R^8$, and $R^9$ are each methyl or H.

A preferred group of compounds of the immediately foregoing compounds is where $R^{10}$ is OH, amino, $OS(O)_2R^{18}$, $OC(O)NR^{20}R^{21}$ or $OS(O)_2NR^{31}R^{32}$.

A preferred group of compounds of the immediately foregoing compounds is where $R^4$, $R^5$ and $R^6$ are each H.

A preferred group of compounds of the immediately foregoing compounds is where Z is hydrogen, halo or $C(O)NR^{20}R^{21}$.

A preferred group of compounds of the immediately foregoing compounds is where Y is H, methyl, S(O)$_2$R$^{18}$, C(O)R$^{19}$, C(O)NR$^{20}$R$^{21}$, C(O)OR$^{24}$ or S(O)$_2$NR$^{31}$R$^{32}$.

A preferred group of compounds of the immediately foregoing compounds is where said compounds are of the formula:

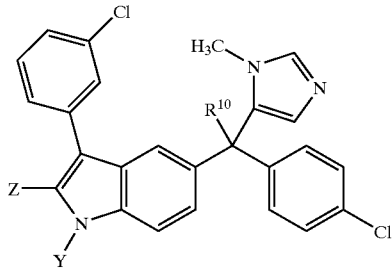

wherein

Z is H, R$^{10}$ is OH and Y is H;
Z is H, R$^{10}$ is NH$_2$ and Y is —S(O)$_2$—CH$_3$;
Z is H, R$^{10}$ is OH and Y is —S(O)$_2$—CH$_3$;
Z is H, R$^{10}$ is OH and Y is —C(O)—N(CH$_3$)$_2$;
Z is H, R$^{10}$ is NH$_2$ and Y is —C(O)—N(CH$_3$)$_2$;
Z is H, R$^{10}$ is NH$_2$ and Y is H;
Z is H, R$^{10}$ is OH and Y is

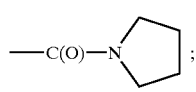

Z is H, R$^{10}$ is NH$_2$ and Y is

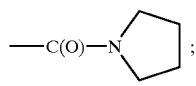

Z is H, R$^{10}$ is OH and Y is —S(O)$_2$-Phenyl;
Z is H, R$^{10}$ is NH$_2$ and Y is —S(O)$_2$-Phenyl;
Z is H, R$^{10}$ is OH and Y is —C(O)—N(CH$_2$CH$_3$)$_2$;
Z is H, R$^{10}$ is NH$_2$ and Y is —C(O)—N(CH$_2$CH$_3$)$_2$;
Z is H, R$^{10}$ is OH and Y is —CH$_3$;
Z is H, R$^{10}$ is NH$_2$ and Y is —CH$_3$;

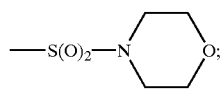

Z is H, R$^{10}$ is OH and Y is
Z is H, R$^{10}$ is NH$_2$ and Y is

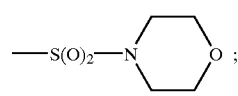

Z is H, R$^{10}$ is OH and Y is

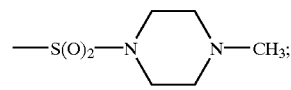

Z is H, R$^{10}$ is NH$_2$ and Y is

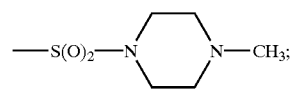

Z is H, R$^{10}$ is OH and Y is

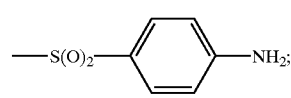

Z is H, R$^{10}$ is NH$_2$ and Y is

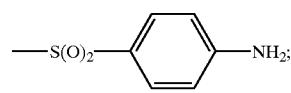

Z is H, R$^{10}$ is OH and Y is —C(O)—CH$_3$;
Z is H, R$^{10}$ is NH$_2$ and Y is —C(O)—CH$_3$;
Z is H, R$^{10}$ is OH and Y is —S(O)$_2$—CF$_3$;
Z is H, R$^{10}$ is NH$_2$ and Y is —S(O)$_2$—CH$_2$—CF$_3$;
Z is H, R$^{10}$ is OH and Y is —S(O)$_2$—CH$_2$—CF$_3$;
Z is H, R$^{10}$ is NH$_2$ and Y is —S(O)$_2$—CH$_2$—CF$_3$;
Z is H, R$^{10}$ is OH and Y is

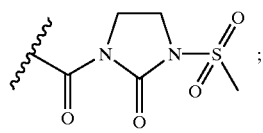

Z is H, R$^{10}$ is NH$_2$ and Y is

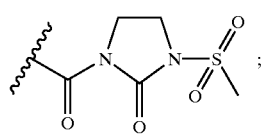

Z is H, R$^{10}$ is OH and Y is

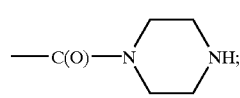

Z is H, R$^{10}$ is NH$_2$ and Y is

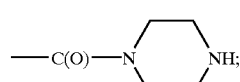

Z is H, R$^{10}$ is OH and Y is

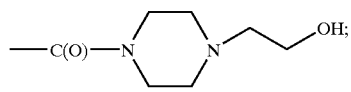

Z is H, R$^{10}$ is NH$_2$ and Y is

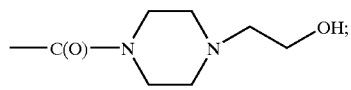

Z is H, R$^{10}$ is OH and Y is

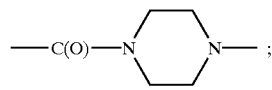

Z is H, R$^{10}$ is NH$_2$ and Y is

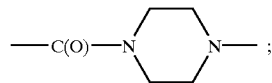

Z is H, R$^{10}$ is OH and Y is —C(O)—NH$_2$;
Z is H, R$^{10}$ is NH$_2$ and Y is —C(O)—NH$_2$;
Z is H, R$^{10}$ is OH and Y is

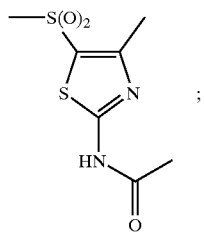

Z is H, R$^{10}$ is NH$_2$ and Y is

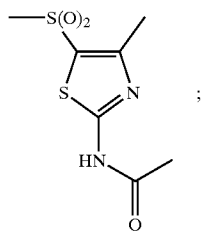

Z is Cl, R$^{10}$ is NH$_2$ and Y is

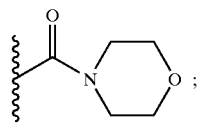

Z is Cl, R$^{10}$ is NH$_2$ and Y is —S(O)$_2$—CH$_3$;

Z is H, R$^{10}$ is OH and Y is

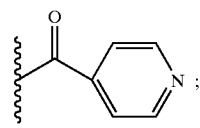

Z is H, R$^{10}$ is NH$_2$ and Y is

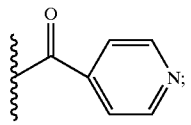

Z is H, R$^{10}$ is OH and Y is

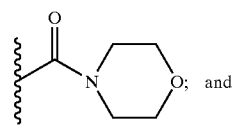; and

Z is H, R$^{10}$ is NH$_2$ and Y is

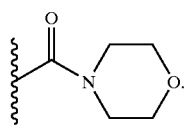.

A preferred group of compounds of the immediately foregoing compounds is where said compounds are of the formula:

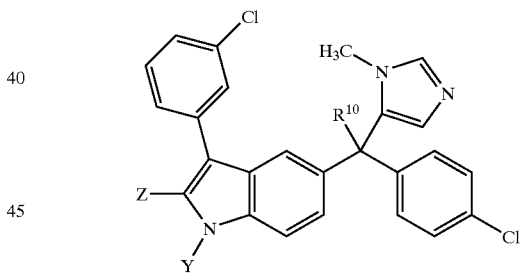

wherein
Z is H, R$^{10}$ is OH and Y is H;
Z is H, R$^{10}$ is NH$_2$ and Y is —S(O)$_2$—CH$_3$;
Z is H, R$^{10}$ is OH and Y is —S(O)$_2$—CH$_3$;
Z is H, R$^{10}$ is OH and Y is —C(O)—N(CH$_3$)$_2$;
Z is H, R$^{10}$ is OH and Y is —C(O)—CH$_3$; and
Z is H, R$^{10}$ is NH$_2$ and Y is —C(O)—CH$_3$.

In another aspect, this invention provides a pharmaceutical composition comprising an effective amount of a compound of formula (I) or (II), as defined hereinabove, or a pharmaceutically acceptable salt thereof and a pharmaceutically acceptable carrier.

In yet another aspect, this invention provides a method of treating a tumor, fibrosis or restenosis in a subject in need thereof, which comprises administering to said subject an effective amount of a compound of formula (I) or (II), as defined hereinabove, or a pharmaceutically acceptable salt thereof.

In still another aspect, this invention provides a method of inhibiting prenyl transferase in a subject in need thereof, which comprises administering to said subject an effective amount of a compound of formula (I) or (II), as defined hereinabove, or a pharmaceutically acceptable salt thereof.

In yet another aspect, the present invention is directed to a process for synthesizing a compound of formula 3, according to the scheme below, which comprises reacting a compound of formula 1, according to the scheme below, with an arylalkylmagnesium chloride of formula 2, according to the scheme below, in which case $X^3$ is Cl—Mg and p=1–2, or an aryllithium of formula 2, in which case $X^3$ is Li and p=0, in an inert organic solvent, until the reaction is substantially complete,

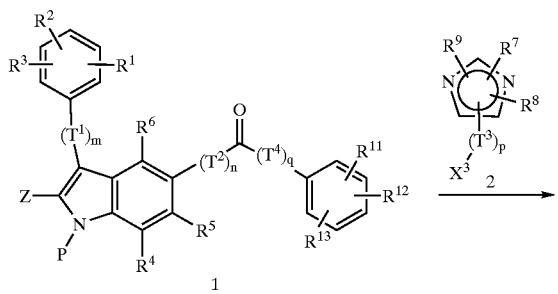

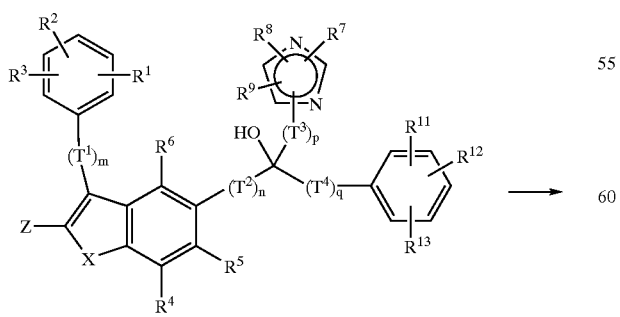

wherein P is a protecting group and the other substituents are as defined for the compound of formula (II) hereinabove.

In still another aspect, the present invention is directed to a process for synthesizing a compound of formula 2, according to the scheme below, which comprises reacting a compound of formula 1, according to the scheme below, with a chlorinating reagent until the reaction is substantially complete,

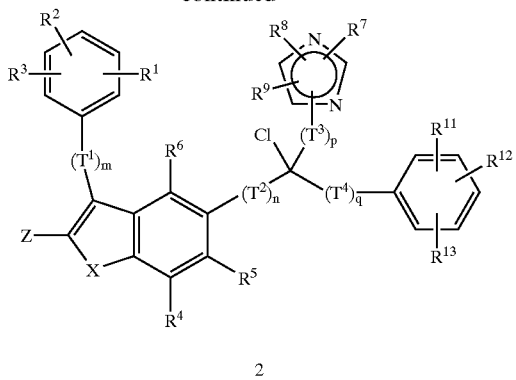

wherein the substituents are as defined for the compound of formula II hereinabove.

In an even further aspect, the present invention is directed to a process for synthesizing a compound of formula 3, according to the scheme below, which comprises reacting a compound of formula 2 with anhydrous liquid ammonia or an inert organic solvent saturated with anhydrous ammonia when n, p and q are each 0, or ammonium hydroxide when n, p and q are each not 0, until the reaction is substantially complete

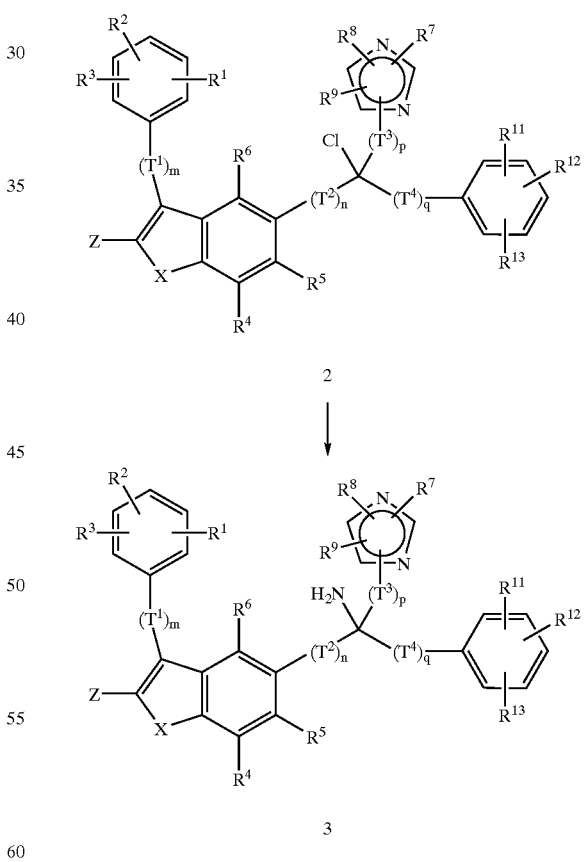

wherein the substituents are as defined for the compound of formula (II) hereinabove.

DETAILED DESCRIPTION

Listed below are definitions of various terms used to describe this invention. These definitions apply to the terms as they are used throughout this specification and claims, unless otherwise limited in specific instances, either individually or as part of a larger group.

In the portion of the compound of formula (I) or (II), where the two optional bonds are shown, only one of the optional bonds may be present in a compound. When the optional bond directly attached to the variable Z is present then Z is an oxygen or sulfur.

The term "alkyl" refers to straight or branched chain unsubstituted hydrocarbon groups of 1 to 20 carbon atoms, preferably 1 to 7 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substitituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected form alkyl, aryl or aralkyl; alkoxycarbonyl, aryl, substituted aryl, guanidino and heterocycles, such as indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic group having 6 to 12 carbon atoms in the ring portion such as phenyl, naphthyl, biphenyl and diphenyl, each of which may be substituted.

The term "arylalkyl" refers to an aryl group bonded directly through an alkyl group, such as benzyl.

The term "substituted aryl" refers to an aryl group substituted by, for example, one to five substituents such as alkyl; substituted alkyl, halo, trifluoromethoxy, trifluoromethyl, hydroxy, alkoxy, alkanoyl, alkanoyloxy, amino, alkylamino, arylalkylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, alkylsulfonyl, sulfonamido, aryloxy and the like. The substituent may be further substituted by hydroxy, alkyl, alkoxy, aryl, substituted aryl, substituted alkyl, or arylalkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to three substituents, such as, aryl, substituted aryl, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated C3–C7 carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", heterocyclic and "heterocyclyl" refer to an optionally substituted, fully saturated or unsaturated, aromatic or non-aromatic cyclic group, for example, which is a 4 to 7 membered monocyclic, 7 to 11 membered bicyclic, or 10 to 15 membered tricyclic ring system, which has at least one heteroatom. Each ring of the heterocyclic group containing a heteroatom may have 1, 2, 3, 4 or 5 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, tetrazolyl and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl) or furo[2,3-b] pyridinyl), dihydroisoindolyl, dihydroquinazoliny (such as 3,4-dihydro-4-oxo-quinazolinyl), benzisothiazolyl, benzisoxaxolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocycles, such as, epoxides and aziridines.

The term "heteroatoms" shall include oxygen, sulfur and nitrogen.

A compound of formula (I) or (II) may form pharmaceutically acceptable salts which are also within the scope of this invention. Pharmaceutically acceptable (i.e. non-toxic, physiologically acceptable) salts are preferred, although other salts are also useful, e.g., in isolating or purifying the compounds of this invention.

A compound of formula (I) or (II) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, with the desired ion in a medium in which the salt precipitates or in an aqueous medium followed by evaporation. Other salts can be formed as known to those skilled in the art.

A compound of formula (I) or (II) may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, tartrates, citrates, succinates, benzoates, ascorbates, salicylates and the like). Such salts may be formed by reacting a compound of formula (I) or (II) in an equivalent amount of the acid in a medium in which the salt precipitates or in an aqueous medium followed by evaporation.

As is well known to those skilled in the art, the known and potential uses of prenyl transferase inhibitors are varied and multitudinous, such as for treating restenosis or a tissue proliferative disease. Examples of tissue proliferative disease include both those associated with benign cell proliferation such as fibrosis, benign prostatic hyperplasia, atherosclerosis and restenosis; and those associated with malignant cell proliferation such as cancer (e.g., ras mutant tumors). Examples of such tumors include breast, colon, pancreas, prostate, lung, ovarian, epidermal and hematopoietic cancers (Sepp-Lorenzino, I, et al., Cancer Research, 55:5302, 1995). Other diseases and conditions that prenyl transferase inhibitors can be used for is in the treatment of neoplasm, fungal infection, arteriosclerosis, retina disease, hepatitis, renal disease, myeloid leukemia, viral infection, nervous system tumor and viral infection.

Accordingly, the present invention includes within its scope pharmaceutical compositions comprising, as an active ingredient, at least one of the compounds of Formula I in association with a pharmaceutically acceptable carrier.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and cornoil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range is 0.01 to 100.0 mg/kg of body weight daily which can be administered as a single dose or divided into multiple doses.

A compound of formula (I) or (II) can be tested for activity as an inhibitor of prenyl transferase according to the following in vitro assay.

Farnesyl transferase activity is assayed by [$^3$H] farnesylation of recombinant human H-Ras protein wild type, using microplate and filtration method. Incubation mixture contains, in a total volume of 25 $\mu$l: 50 mM Tris HCl (pH 7.5), 5 mM dithiothreitol, 20 $\mu$M ZnCl$_2$, 40 mM MgCl$_2$, 0.6 $\mu$M [$^3$H] farnesyl pyrophosphate (22.3 Ci/mmol), 4 $\mu$M H-Ras and 10 $\mu$g of farnesyl transferase from human brain cytosol. Test compounds are added in adequate solvent and incubations start by addition of farnesyl transferase. After approximately 60 minutes at approximately 37° C., the reaction is stopped by addition of 100 μl of 10% HCl in ethanol and allowed to incubate approximately 15 minutes at approximately 37° C., then 150 μl of absolute ethanol are added and incubation mixture is filtered on Unifilter GF/B microplates and washed 6 times with ethanol. After addition of 50 μl of Microscint 0, plates were counted on a Packard Top Count scintillation counter. Geranylgeranyl transferase activity is assayed by the same method, but using 4 μM human recombinant H-Ras CVLL type, 0.6 μM [$^3$H] geranylgeranyl-pyrophosphate (19.3 Ci/mmol) and 100 μg of geranylgeranyltransferase from human brain.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

The compounds of the present invention can be made according to the following schemes and associated descriptions and by methods well-known to those of ordinary skill in the art. The starting materials and reagents are either commercially available or can be synthesized according to published procedures well-known to those of ordinary skill in the art. The substituents have the same definitions as for the compound of formula (II), shown hereinabove.

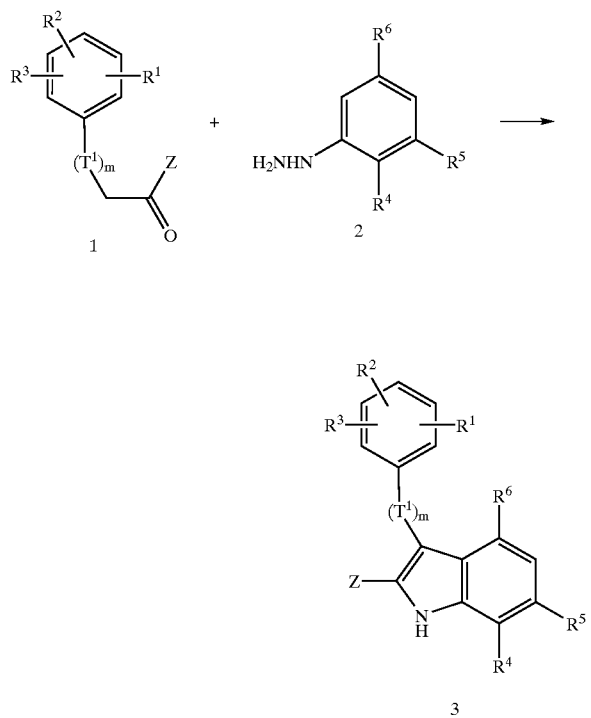

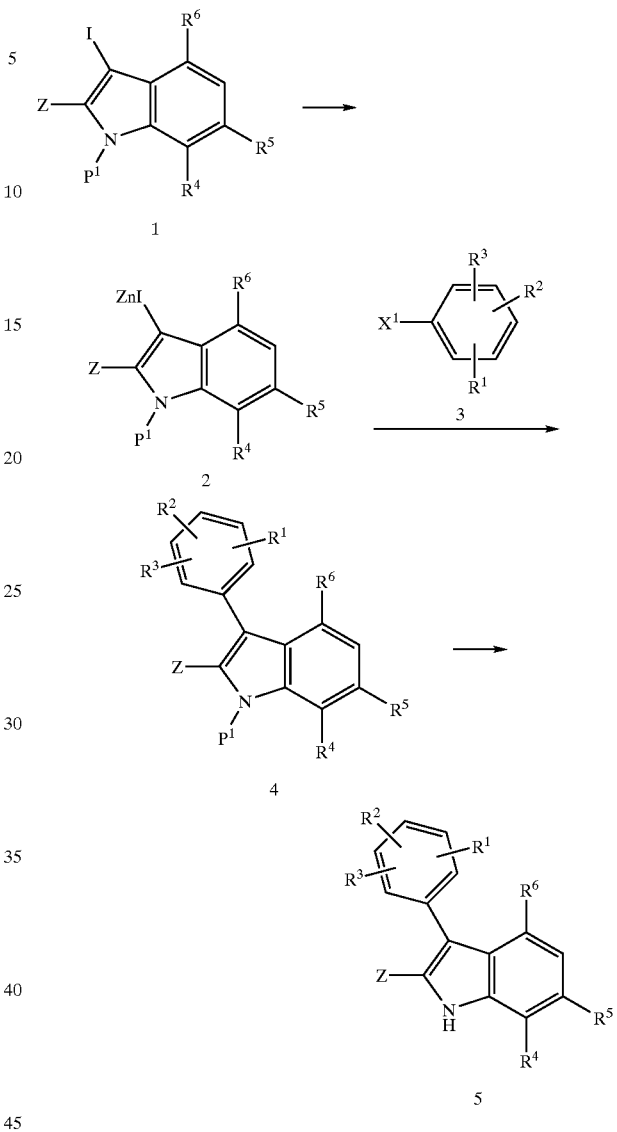

This reaction is accomplished by the reaction of an aldehyde or ketone of formula 1 with a phenylhydrazine of formula 2 in a mixed acid/organic solvent or an acid solvent, such as acetic acid at an elevated temperature, preferably at reflux temperatures.

Step 1

In Scheme 2, starting material 1 has a protecting group, P$^1$, such as a phenylsulfonyl or methylsulfonyl group, at position 1 of the indole ring. An indole of formula 1 is treated in an organic solvent, such as tetrahydrofuran, with active zinc at about room temperature to give 3-indolylzinc iodide 2.

Step 2

Thereafter product 2 is coupled with an iodo- or bromo-aromatic system 3 (X$^1$=I or Br), such as iodobenzene in the presence of a catalyst, such as tetrakis(triphenylphosphine) palladium in an organic solvent at about room temperature.

Step 3

Thereafter product 3 is hydrolyzed by using an appropriate base, such as KOH or NaOH in a suitable solvent, such as methanol at from about 0° C. to about 100° C. This step may also be accomplished by treating with tetraalkylammonium fluoride, such as tetrabutylammonium fluoride in a suitable organic solvent, such as tetrahydrofuran, at an elevated temperature, preferably reflux temperatures.

Scheme 3

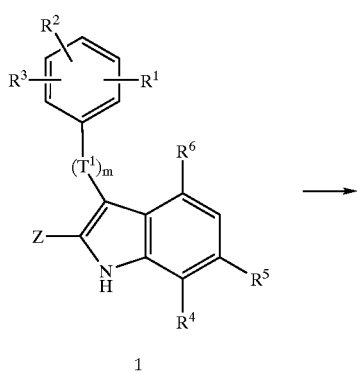

1

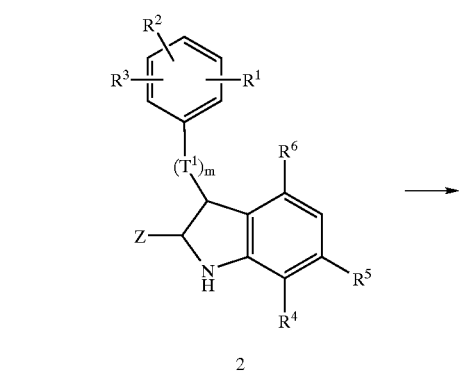

2

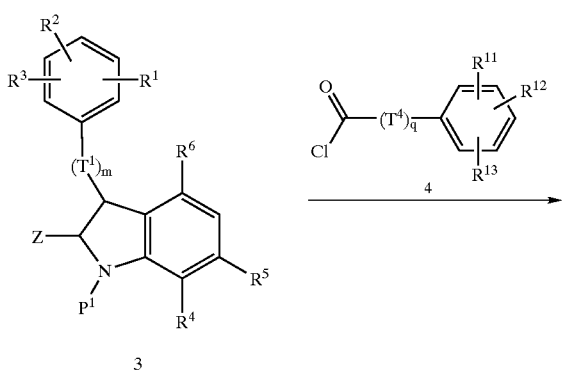

3

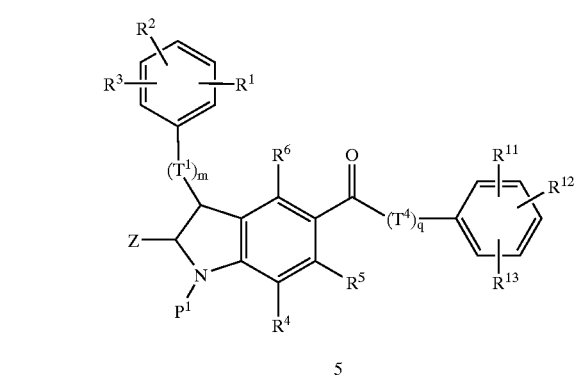

5

Step 1

In Scheme 3, compound 1 is reduced by using an appropriate reducing agent, such as borane in an organic solvent containing a suitable acid, such as tetrahydrofuran containing trifluoroacetic acid at from about 0° C. to about room temperature.

Step 2

Thereafter product 2 is protected by reacting with an appropriate agent, such as methanesulfonyl chloride, p-toluenesulfonyl chloride or phenylsulfonyl chloride in the presence of a base, such as triethylamine or N,N-diisopropylethylamine in an inert organic solvent, such as dichloromethane or N,N-dimethylformamide at from about −78° C. to about room temperature.

Step 3

Thereafter product 3 is coupled with the chloride acid 4 in the presence of an acid or Lewis acid, such as aluminum chloride, in a solvent, such as carbon disulfide or dichloromethane at from about −78° C. to an elevated temperature such as 100° C.

Scheme 4

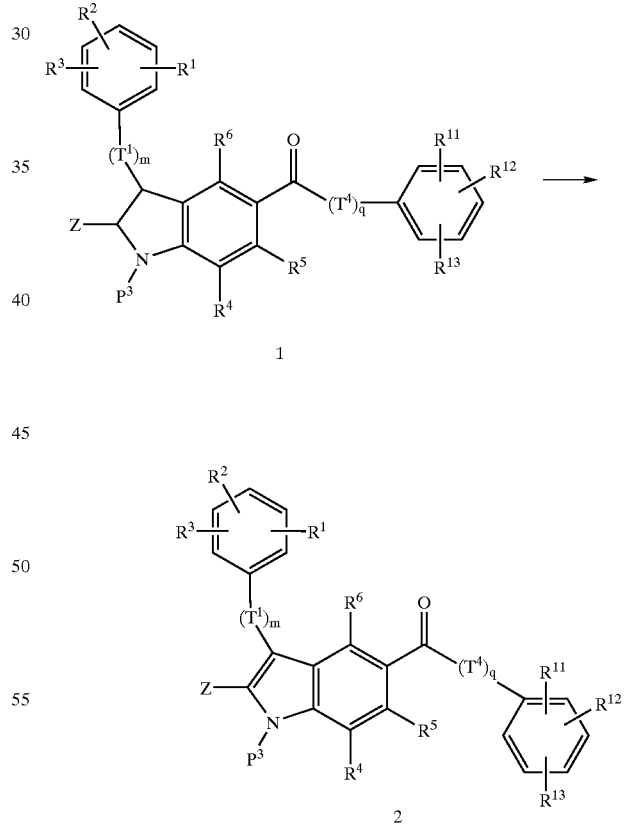

In Scheme 4, compound 1 is oxidized by reacting it with an oxidizing agent, for example, 2,3-dichloro-5,6-dicyano-1,4-benzoquinone or manganese (III) acetate dihydrate in an organic solvent, such as dioxane or acetic acid from about room temperature to about 150° C.

Scheme 5

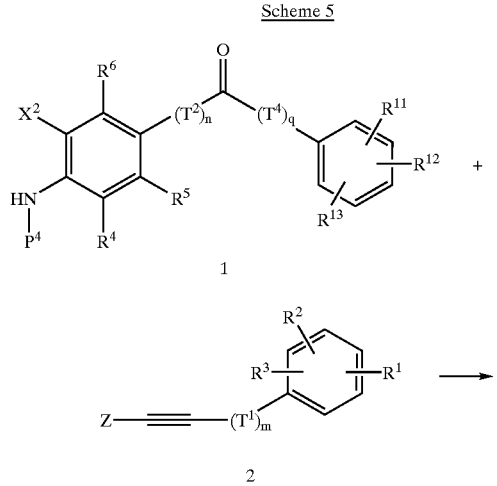

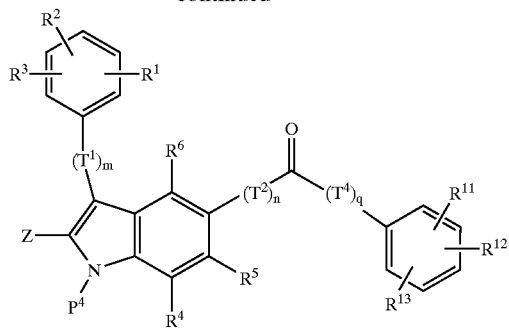

In Scheme 5, compound 1 which has an iodo- or bromo-substituent at position 2 ($X^2$=I or Br) is reacted with an alkyne 2 in the presence of a suitable catalyst, such as palladium(II) acetate, an appropriate base such as potassium carbonate and other agents which are necessary for the reaction, such as triphenylphosphine/lithium chloride in an organic solvent, such as N,N-dimethylformamide at from about room temperature to about 150° C.

Scheme 6

Step 1

In scheme 6, compound 1 is treated with nitrous acid in a solvent, such as water or sulfuric acid at from about 0° C. to 50° C.

Step 2

Thereafter product 2 is reacted with compound 3 in the presence of a suitable base, such as potassium hydroxide in a solvent such as water at about 0° C. The mixture is treated with an acid, such as ethanolic hydrogen chloride at from about 50° C. to about 80° C.

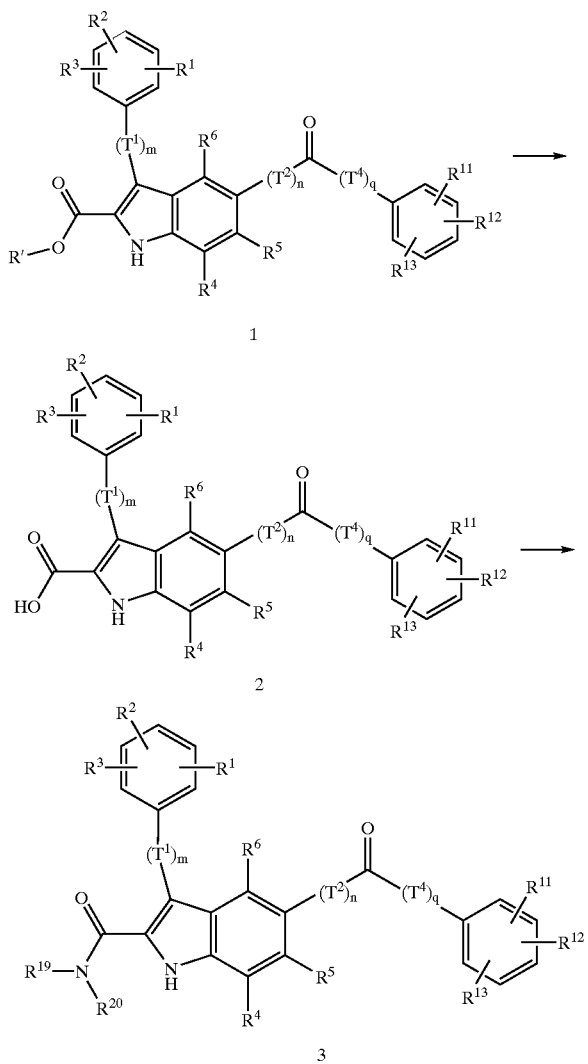

Step 1

In Scheme 7, compound 1 is hydrolyzed by reacting with a base, such as potassium hydroxide or sodium hydroxide in a solvent mixture, such as water/ethanol or a solvent, such as ethanol or water at an elevated temperature, preferably at reflux temperatures.

Step 2

Thereafter product 2 is reacted with a primary or secondary amine in the presence of a coupling agent such as 2-(1H-benzotriazole-1-yl)-1,1,3,3-tetramethyluronium hexafluorophosphate and a base, such as diisopropylethylamine in an organic solvent, such as N,N-dimethylformamide at from about 0° C. to about room temperature.

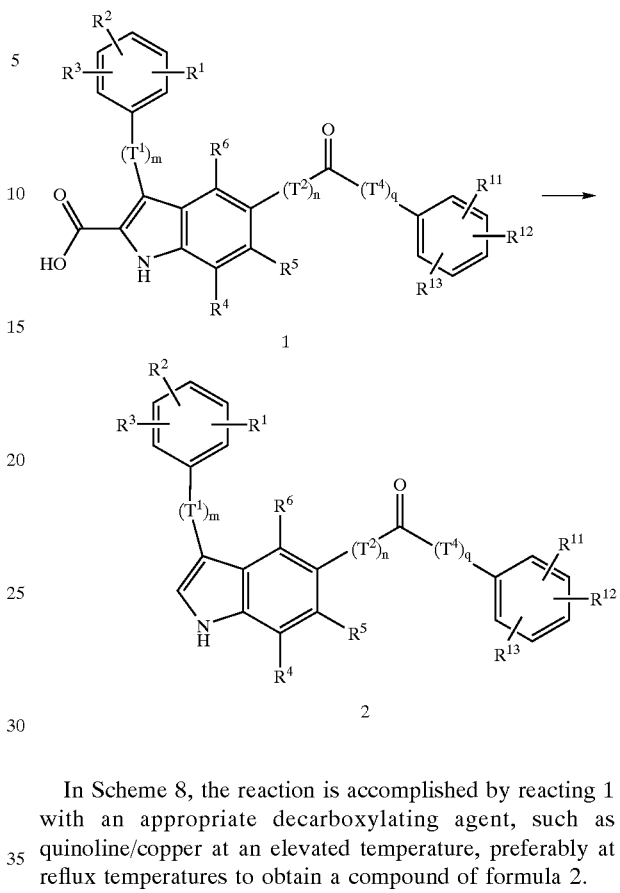

In Scheme 8, the reaction is accomplished by reacting 1 with an appropriate decarboxylating agent, such as quinoline/copper at an elevated temperature, preferably at reflux temperatures to obtain a compound of formula 2.

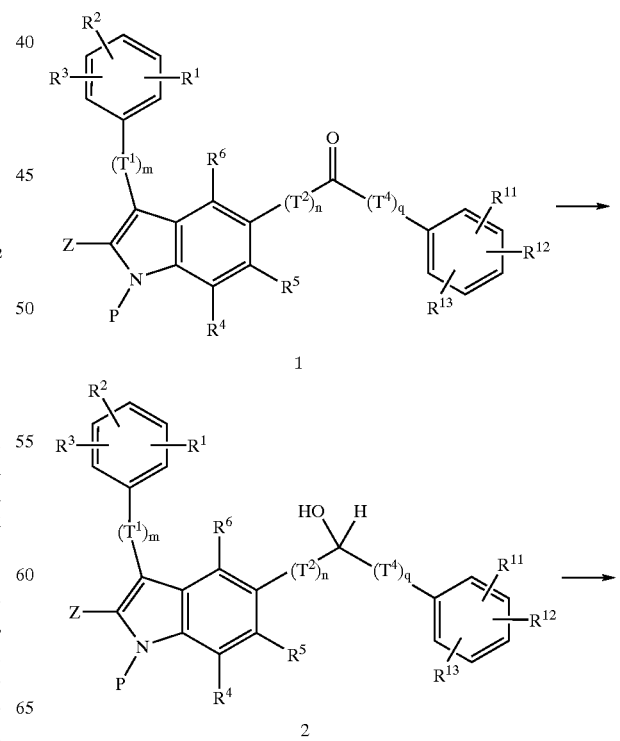

-continued

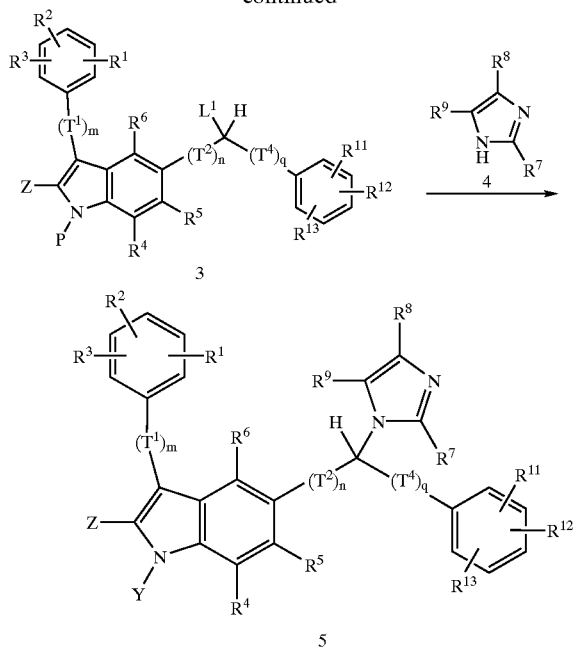

Step 1
In Scheme 9, compound 1 is reduced by reacting with a suitable reducing agent, such as sodium borohydride in a suitable organic solvent, such as ether or tetrahydrofuran, yielding intermediate 2.

Step 2
Thereafter product 2 is reacted with an appropriate reagent, such as thionyl chloride or methanesulfonyl chloride to convert the hydroxy group into an active leaving group, such as chloro- or methylsulfonate group ($L^1$=Cl or $CH_3S(O)_2O$—).

Step 3
Thereafter product 3 is reacted with an imidazole of formula 4 in the presence of a suitable base, such as potassium carbonate in an organic solvent, such as acetonitrile at an elevated temperature, preferably at reflux temperatures. If the optional protecting group P is not stable under the reaction condition and hydrolyzed, another additional step may be needed to introduce the Y group at the nitrogen in the indole ring. If this additional step is required, the intermediate is treated with Y—L, in which L is an active leaving group, for example Y—Cl, e.g., methanesulfonyl chloride or dimethylcarbamoyl chloride, in an inert organic solvent at from about −78° C. to about room temperature.

Scheme 10

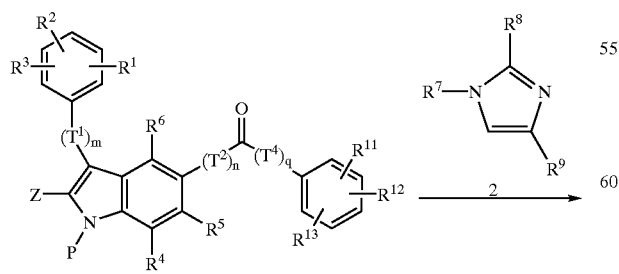

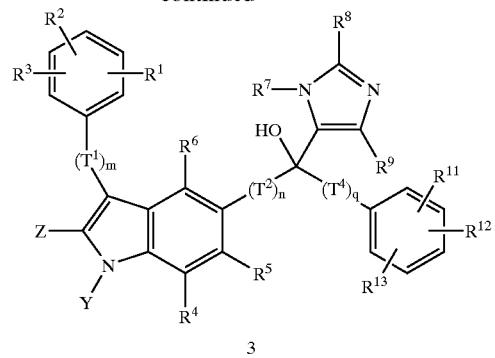

In Scheme 10, compound 1 is reacted with an imidazole of formula 2, in which $R^7$ is an optional protective group, such as a dimethylamino sulfonyl group, which can be removed after the addition. The reaction takes place in the presence of a suitable base, such as butyl lithium. If $R^8$ is hydrogen at position 2 of the imidazole then it needs to be temporarily protected with a protecting group, such as triethylsilane by reacting it with an appropriate reagent, such as chlorotriethylsilane. If the optional protective group P, such as a methylsulfonyl group is not stable under the reaction condition and cleaved off, another reagent which can introduce a Y group at the nitrogen of the indole ring, for example Y—Cl, e.g., methanesulfonyl chloride or dimethylcarbamoyl chloride, may be added into the reaction mixture to obtain the desired compound 3. The chlorotriethylsilyl group is hydrolyzed during the work-up procedure.

Scheme 11

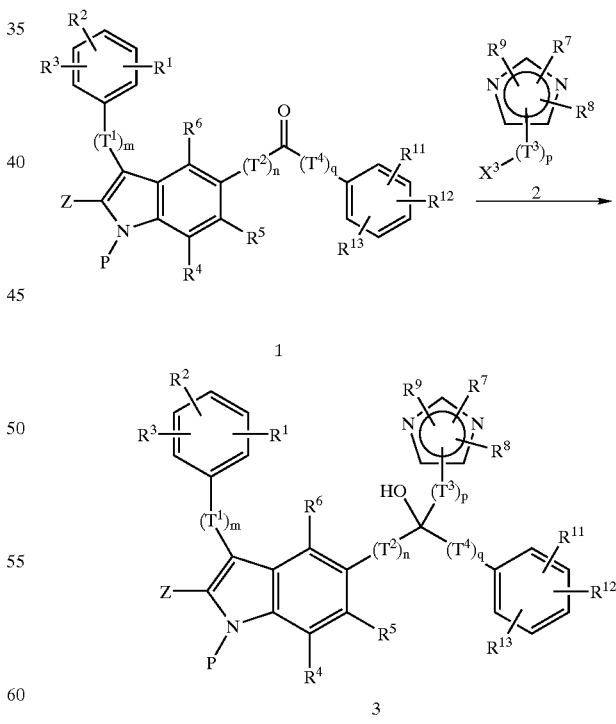

In Scheme 11, compound 1 is reacted with an arylalkylmagnesium chloride ($X^3$=Cl—Mg, p=1–2) or an aryllithium ($X^3$=Li, p=0) shown as compound 2, in an inert organic solvent, such as tetrahydrofuran. If the optional protective group P, is not stable under the reaction condition and cleaved off, another reagent which can introduce a Y group at the nitrogen of the indole ring, for example Y—Cl, e.g., methanesulfonyl chloride or dimethylcarbamoyl chloride, may be added into the reaction mixture to obtain the desired compound 3.

Step 1

In Scheme 12, the first reaction is accomplished by the reaction of an aldehyde or ketone of formula 1 with a phenylhydrazine or its derivative of formula 2 in a mixed acid/organic solvent or an acid solvent, such as acetic acid at an elevated temperature, preferably at reflex temperature.

Step 2

Thereafter product 3 is reacted with Y—L, in which L is an active leaving group, such as a chloride group, in the presence of a suitable base, such as triethylamine or diisopropylethylamine in an inert organic solvent, such as dichloromethane or N,N-dimethylformamide at from about −78° C. to about room temperature.

Step 3

Thereafter product 4 is converted into alkyl- (n=1 or 2) or arylmagnesium (n=0, M=MgX$^3$, in which X$^3$=halide, e.g., Cl or Br) halide or alkyl-(n=1 or 2) or aryl-(n=0, M=Li) lithium by reacting with metallic magnesium, lithium metal or alkyllithium, such as butyllithium in an inert organic solvent, such as ether or tetrahydrofuran at about −12° C. to about room temperature.

Step 4

Thereafter product 5 is reacted with ketone 6 in an inert organic solvent, such as ether or tetrahydrofuran at from about −12° C. to about room temperature.

Scheme 12

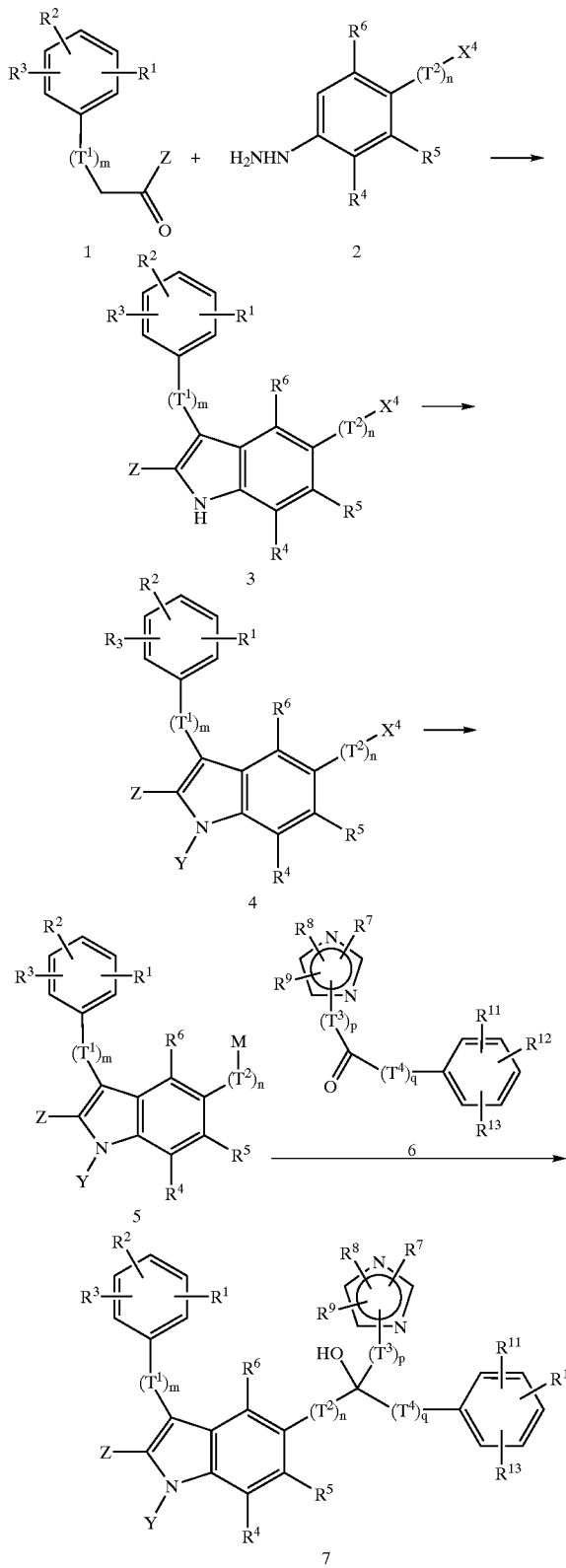

Scheme 13

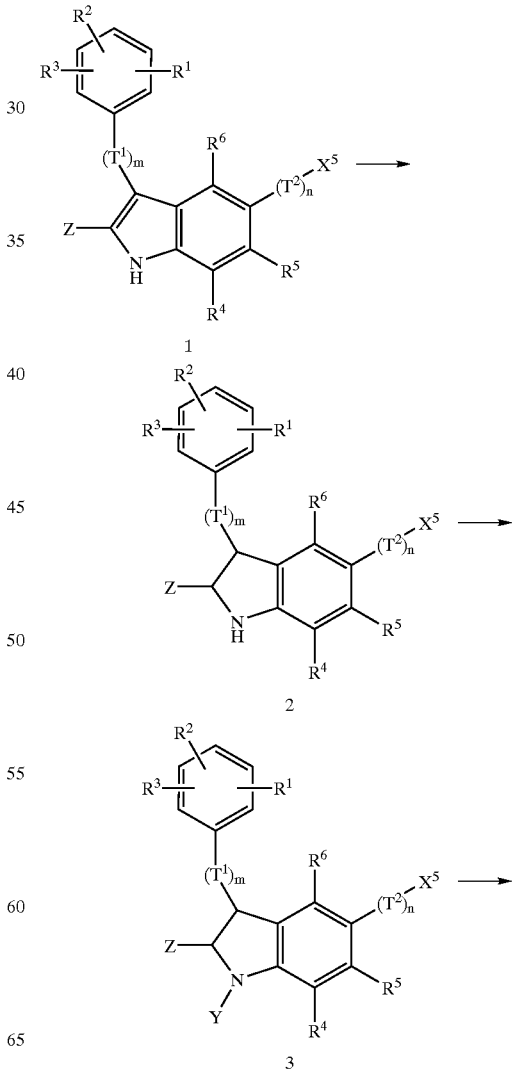

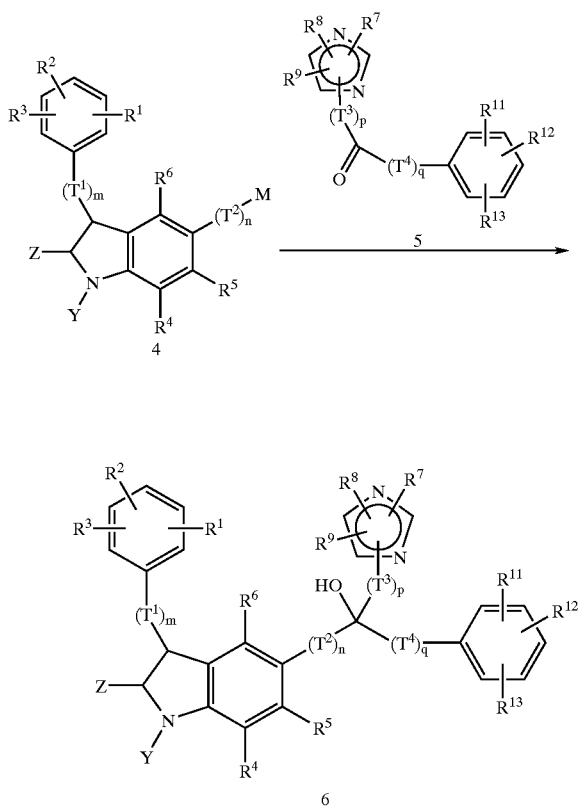

Step 1

In Scheme 13, starting material 1 is reduced by reacting with a reducing agent, such as borane in an organic solvent, such as tetrahydrofuran containing an acid, such as trifluoroacetic acid at from about 0° C. to about room temperature.

Step 2

Thereafter product 2 is reacted with Y—L, in which L is an active leaving group, such as a chloro group, in the presence of a suitable base, such as triethylamine or diisopropylethylamine in an organic solvent, such as dichloromethane or N,N,-dimethylformamide at from about −78° C. to about room temperature, yielding compound 3.

Step 3

Thereafter product 3 is converted into alkyl-(n=1 or 2) or arylmagnesium (n=0, M=MgX$^5$, in which X$^5$=halide, e.g., Cl or Br) halide or alkyl-(n=1 or 2) or aryl-(n=0) lithium (M=Li) by reacting with metallic magnesium, lithium metal or alkyllithium, such as butyllithium in an inert organic solvent, such as ether or tetrahydrofuran at about −12° C. to about room temperature.

Step 4

Thereafter product 4 is reacted with ketone 5 in an inert organic solvent, such as ether or tetrahydrofuran at from about −12° C. to about room temperature.

In Scheme 14, compound 1 can be converted to compound 2 by reacting with a suitable group of reagents, such as methyl sulfoxide/concentrated HCl or potassium persulfate/sodium acetate in a suitable solvent such as water or an alcohol.

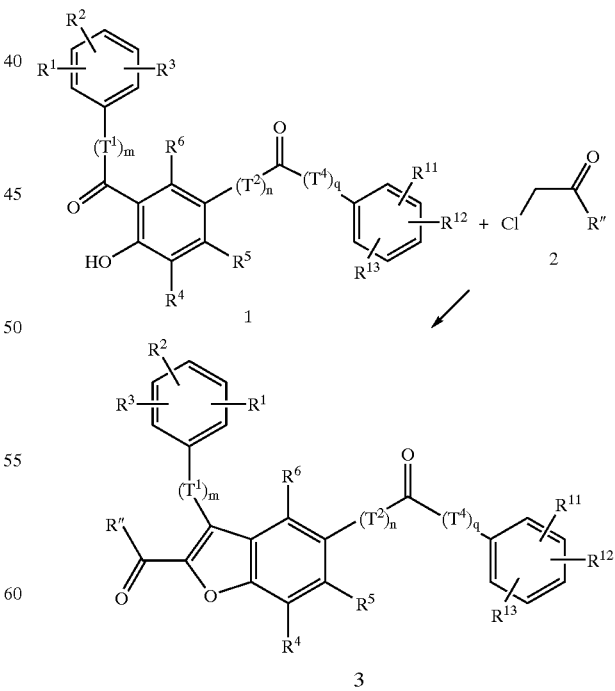

In Scheme 15, compound 1 can be convened to compound 3 by reacting with compound 2 in the presence of suitable base.

Scheme 16

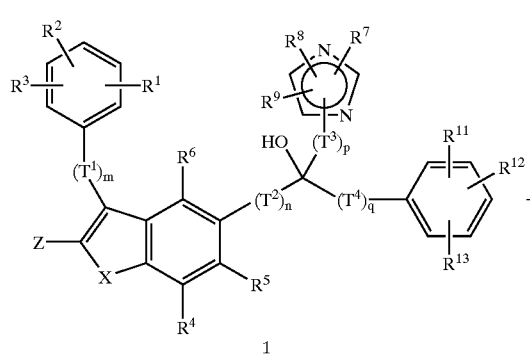

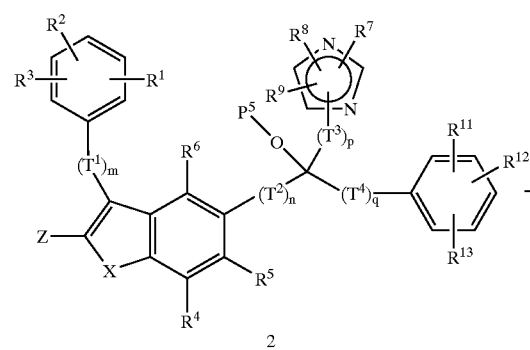

In Scheme 16, compound 1 can be converted to compound 3 by reacting it with compound 2 under suitable conditions.

Scheme 17

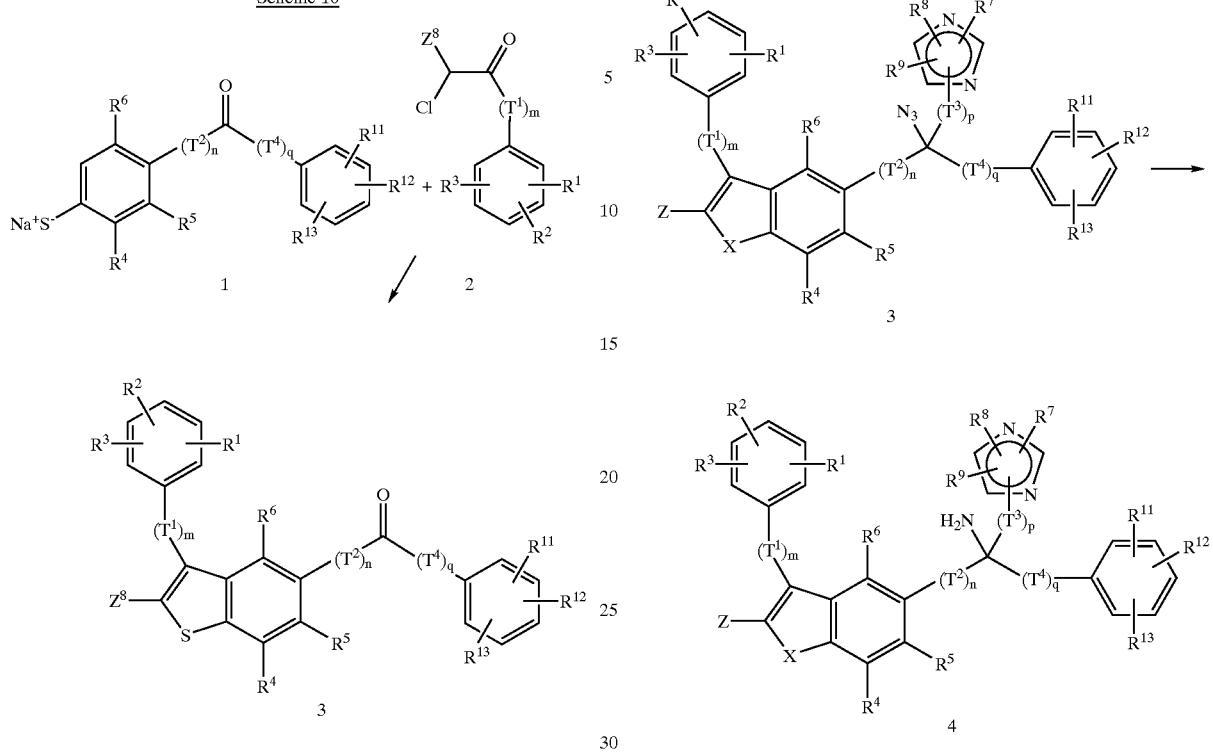

Step 1

In Scheme 17, compound 1 is converted to compound 2, in which $P^4$—O— is an active leaving group, such as methylsulfonate, p-toluenesulfonate or trifluoromethanesulfonate by reacting it with a suitable reagent, such as methanesulfonyl chloride, ρ-toluenesulfonyl chloride or trifluoromethanesulfonic anhydride in an inert organic solvent, such as dichloromethane.

Step 2

Thereafter product 2 is reacted with sodium azide to yield compound 3 in an organic solvent, such as N,N-dimethylformamide at from about room temperature to an elevated temperature, such as about 60° C.

Step 3

Thereafter product 3 is reduced to compound 4 by reacting it with an appropriate reducing agent, such as triphenylphosphine with water in a suitable solvent such as pyridine.

Scheme 18

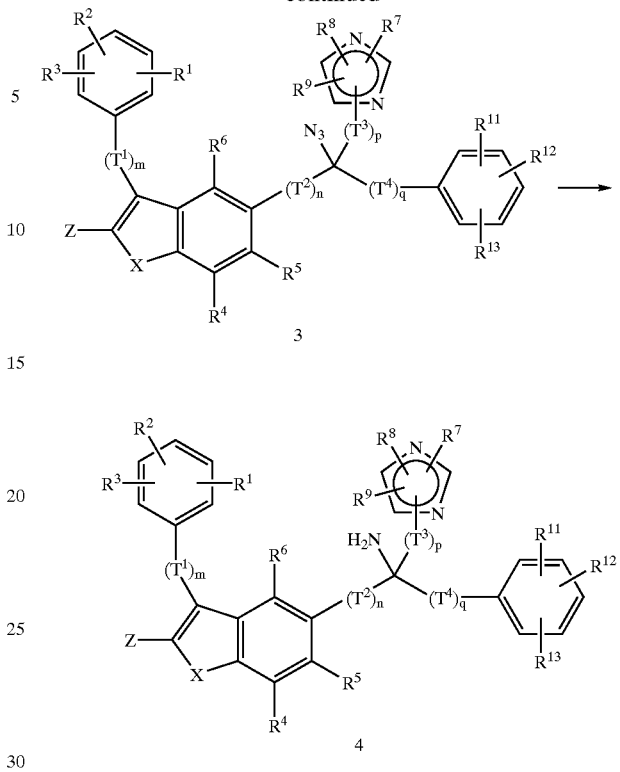

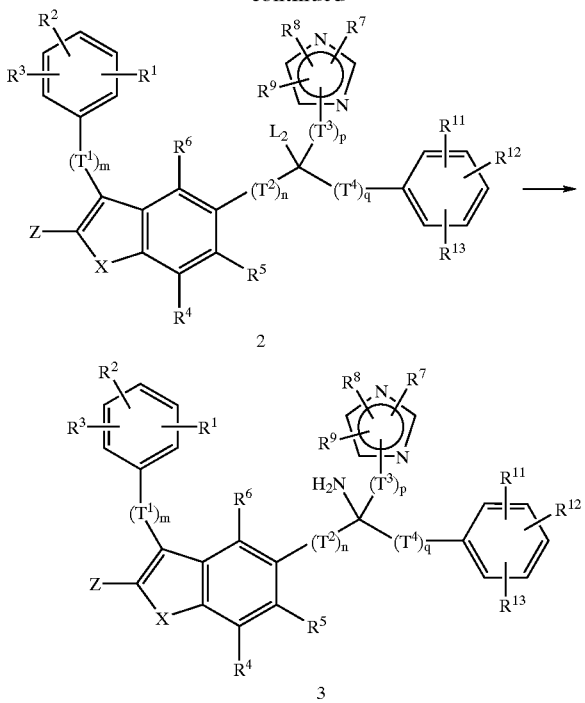

Step 1

In Scheme 18, compound 1 can be converted to compound 2 which has an active leaving group, such as a chloro group, by reacting with an appropriate reagent, such as thionyl chloride at from about room temperature to an elevated temperature, preferably at about 38° C.

Step 2

Thereafter product 2 is reacted with an appropriate agent, such as liquid ammonia at from low temperature, such as −78° C., to an elevated temperature.

EXAMPLE 1

(±)-3-(3-Chlorophenyl)-5-[(4-chlorophenyl)hydroxyl (1-methyl-1H-imidazol-5-yl)methyl]Indole To a solution of 1-methylimidazole (53 mg) in anhydrous THF (3 mL) was added dropwise a solution of butyllithium in hexane (1.6 M, 430 μL) at about −78° C. The mixture was stirred at about −78° C. for about 15 minutes. To the solution was added dropwise a solution of chlorotriethylsilane in THF (1.0M, 660 μL). The mixture was warmed to room temperature and stirred at room temperature for 1 hour. The mixture was cooled to about −78° C. and to it was added dropwise a solution of butyllithium in hexane (1.6M, 430 μL). The solution was stirred at about −78° C. for about 1 hour and in the following 15 minutes, it was warmed to about −15° C. The solution was cooled to about −78° C. To it was added dropwise a solution of 1-methylsulfonyl-3-(3-chlorophenyl)-5-(4-chlorobenzoyl)indole (95 mg) (see preparation #7) in THF (2 mL). The mixture was warmed to room temperature and stirred for about 2 hours. The solution was cooled to about 0° C. and to it was added methanol and water. The mixture was stirred for about 2 hours. The solution was concentrated in vacuo. The residue was dissolved in dichloromethane (DCM) and washed with water once. The organic layer was dried over anhydrous MGSO$_4$, filtered, and concentrated in vacuo. The crude product was purified by column chromatography, on silica, eluting with DCM/MeOH 95:5. Affording the title compound Rf=0.20 (silica, DCM/MeOH 9:1), MS (ES) 447.2; Calc. MW=447.4. 60 mg, yield: 63%.

Alternatively, the compound of Example 1, (±)-3-(3-chlorophenyl)-5-[(4-chlorophenyl)hydroxy(1-methyl-1H-imidazol-5-yl)methyl]indole can be synthesized according to the following procedure. To a solution of 1-methylimidazole (53 mg) in anhydrous THF (3 mL) was added dropwise a solution of butyllithium in hexane (1.6 M, 430 μL) at about −78° C. The mixture was stirred at about −78° C. for about 15 minutes. To the solution was added dropwise a solution of chlorotriethylsilane in THF (1.0M, 660 μL). The mixture was warmed to room temperature and stirred at room temperature for about 1 hour. The mixture was cooled to about −78° C. and to it was added dropwise a solution of butyllithium in hexane (1.6M, 430 μL). The solution was stirred at about −78° C. for about 1 hour and in the following 15 minutes, it was warmed to about −15° C. The solution was cooled to about −78° C. To it was added dropwise a solution of 1-methylsulfonyl-3-(3-chlorophenyl)-5-(4-chlorobenzoyl)indoline (95 mg) (see preparation #6) in THF (2 mL). The mixture was warmed to room temperature and stirred for about 2 hours. The solution was cooled to about 0° C. and to it was added methanol and water. The mixture was stirred for about 2 hours. The solution was concentrated in vacuo. The residue was dissolved in dichloromethane (DCM) and washed with water once. The organic layer was dried over anhydrous MgSO$_4$, filtered and concentrated in vacuo. The crude product was purified by column chromatography on silica gel eluting with DCM/MeOH 95:5, affording the title compound.

The enantiomers of the title compound can be separated by using techniques known in the art, such as prep HPLC over a chiral column.

EXAMPLE 2

(±)-1-Methylsulfonyl-3-(3-chlorophenyl)-5-[(4-chlorophenyl)hydroxy(1-methyl-1H-imidazol-5-yl) methyl]indole To a solution of 1-methylimidazole (88 mg) in anhydrous THF (3 mL) was added dropwise a solution of butyllithium in hexane (1.6 M, 694 μL) at about −78° C. The mixture was stirred at about −78° C. for about 15 minutes. To the solution was added dropwise a solution of chlorotriethylsilane in THF (1.0 M, 1.08 mL). The mixture was warmed to room temperature and stirred for about 1 hour. The solution was cooled to about −78° C. To it was added dropwise a solution of butyllithium in hexane (1.6 M, 694 μL). The mixture was stirred at about −78° C. for about 1 hour and then warmed to about −15° C. It was stirred at about −15° C. for about 15 minutes. The solution was cooled to about −78° C. To the solution was added dropwise a solution of 1-methylsulfonyl-3-(3-chlorophenyl)-5-(4-chlorobenzoyl)indoline (150 mg) (see preparation #6) in THF (2 mL). The mixture was warmed to room temperature and stirred for about 2 hours. The solution was cooled to about −78° C. To it was added dropwise methanesulfonyl chloride (116 mg). The solution was slowly warmed to room temperature and stirred overnight. The solution was cooled to about 0° C. To it was added water and stirred for about 2 hours. The solution was diluted with DCM and the organic layer was separated and concentrated in vacuo. The crude product was purified by column chromatography on silica, eluting with CHCl$_3$/MeOH 95:5 affording the title compound as a solid. MS (ES): 525.1; Calc. MW=525.5. 30 mg, yield: 17%.

Alternatively, the compound of Example 2, (±)-1-Methylsulfonyl-3-(3-chlorophenyl)-5-[(4-chlorophenyl)

hydroxy(1-methyl-1H-imidazol-5-yl)methyl]indole can be synthesized according to the following procedure.

To a solution of 1-methylimidozole (88 mg) in anhydrous THF (1.5 mL) was added dropwise a solution of butyllithium in hexane (1.6M, 694μL) at about −78° C. The mixture was stirred at about −78° C. for about 30 min. To the solution was added dropwise a solution of chlorotriethylsilane in THF (1.0M, 1.11 mL). The mixture was warmed to room temperature and stirred at room temperature for about 1 hour. The solution was cooled to about −78° C. To it was added dropwise a solution of butyllithium in hexane (1.6M, 694μL). The mixture was stirred at about −78° C. for about 1 hour arid was warmed to about −15° C. during the following 30 min. The solution was cooled to about −78° C. To it was added dropwise of a solution of 1-methylsulfonyl-3-(3-chlorophenyl)-5-(4-chlorobenzoyl)indole (150 mg) (see preparation #7) in THF (lmL). The solution was warmed to room temperature and stirred at room temperature for 19 hours. The solution was cooled to −78° C. To it were added dropwise methanesulfonyl chloride (163 mg), then, diisopropylethylamine (87 mg). The solution was warmed to room temperature in 1 hour and stirred at room temperature for 3 hours. To the solution was added 4 mL of 1N HCl aqueous solution and 4 mL of THF. The solution was stirred at 0° C. for 1.5 hours. The organic solvent was removed in vacuo. The aqueous solution was neutralized to pH=8 by adding 6N KOH aqueous solution at 0° C. The aqueous solution was extracted with DCM twice. The organic layers were combined and washed with brine once, dried over $MgSO_4$, filtered and condensed in vacuo. The residue was purified by column chromatography on silica, eluting with $CH_3Cl/MeOH/Et_3N$, 98:2:0.1 The title compound was obtained as a solid, 44 mg, yield: 25%. MS(ES) 525.2, Calc. MW=525.3.

Alternatively, the compound of Example 2, (±)-1-methylsulfonyl-(3-chlorophenyl)-5-[(4-chlorophenyl) hydroxyl (1-methyl-1H-imidazol-5-yl) methyl] indole was also made analogously to the method described for making Example Y, using methanesulfonyl chloride in place of 4-morpholinecarbonyl chloride. Yield: 77%. MS (Calc.): 526.46, MS(ES): 526.

The enantiomers of the title compound can be separated by using a technique known in the art, such as preparative HPLC on a chiral column.

EXAMPLE 3

(±)-1-(N,N-Dimethylcarbamoyl)-3-(3-chlorophenyl)-5-[(4-chlorophenyl) hydroxy(1-methyl-1H-imidazol-5-yl)methyl]indole The title compound was synthesized analogously to the second method described for making Example 2, using dimethylcarbamyl chloride in place of methanesulfonyl chloride. MS (electrospray):518.2; calc. MW: 518.5.

EXAMPLE 4

(±)-1-Methylsulfonyl-3-(3-chlorophenyl)-5-[amino(4-chloro-phenyl)(1-methyl-1H-imidazol-5-yl)methyl]indole Freshly distilled $SOCl_2$ (18 ml) was injected into (±)-1-methylsulfonyl-3-(3-chlorophenyl)-5-[(4-chlorophenyl) hydroxy (1-methyl-1H-imidazol-yl) methyl]indole (1) (1.74 g, 3.31 mmol, see Example 2) under $N_2$ atmosphere and stirred at about 38° C. for about 21 hrs. The mixture was evaporated to dryness in vacuo. 1.9 g of the intermediate, (±)-1-methylsulfonyl-3-(3-cholorophenyl)-5-[chloro(4-chlorophenyl)(1-methyl-1H-imidazol-yl)methyl]indole, was obtained and it was used in the following reaction without further purification. The crude intermediate was taken into 15 ml THF and injected into 45 mL of liquid $NH_3$ solution under $N_2$ at −78° C. The mixture was stirred for about 2 h and gradually warmed up to room temperature. The reaction solution was diluted by methylene chloride and filtered. The filtrate was evaporated to dryness in vacuo. The crude product was purified by flash chromatograph over silica gel, eluting with a mixture of methylene chloride and MeOH (5/0.2). The pure fractions were pooled and stripped down. The amine was converted into HCl salt and recrystallized from $CH_2Cl_2$/hexane. The precipitate was filtered and dried under vacuum overnight, yielding 1.02 g (56%) of the title compound. MS (Calc.) 525.46, MS (ES):525.2.

EXAMPLE 7

(±)-1-(1-Pyrrolidinecarbamoyl)-3-(3-chlorophenyl)-5-[(4-chlorophenyl)hydroxy(1-methyl-1H-imidazol-5-yl)methyl]indole The title compound was synthesized analogously to the second method described for making Example 2, using 1-pyrrolidinecarbonyl chloride in place of methanesulfonyl chloride. MS (electrospray):544.3; calc. MW: 544.51.

EXAMPLE 11

(±)-1-(N,N-Diethylcarbamoyl)-3-(3-chlorophenyl)-5-[(4-chlorophenyl)hydroxy(1-methyl-1H-imidazol-5-yl)methyl]indole The title compound was synthesized analogously to the second method described for making Example 2, using diethylcarbamyl chloride in place of methanesulfonyl chloride. MS (electrospray):546.2; calc. MW: 546.5.

EXAMPLE 21

(±)-1-Acetyl-3-(3-chlorophenyl)-5-[(4-chlorophenyl)hydroxy(1-methyl-1H-imidazol-5-yl)methyl]indole The title compound was synthesized analogously to the first method described for making example 2, using acetic anhydride in place of methanesulfonyl chloride. MS(electrospray): 489.2; Calc. MW: 489.4.

EXAMPLE V (±)-1-Methylsulfonyl-2-chloro-3-(3-cholorophenyl)-5-[amino(4-chlorophenyl)(1-methyl-1H-imidazol-yl)methyl]indole The title compound was made analogously to the method described in Example 4, except that (±)-1-methylsulfonyl-3-(3-cholorophenyl)-5-[(4-chlorophenyl)hydroxy(1-methyl-1H-imidazol-yl) methyl]indole was reacted with thionyl chloride for about 3 days instead of 21 hrs. Yield: 55%. MS (Calc.):559.91, MS (ES): 559.00.

EXAMPLE Y (+)-1-(4-Morroholinecarbamoyl)-3-(3-chlorophenyl)-5-[(4-chlorophenyl)-hydroxy(1-methyl-1H-imidazol-5-yl)methyl]indole A THF solution (75 ml) of 1-methylimidazole (5.28 ml, 66.12 mmol) was cooled down to about −78° C., to which 2.5 M n-butyllithium in hexane (28.25 ml, 70.628 mmol) was added under $N_2$ atmosphere. The mixture was stirred for about 30 min at about −78° C., then 1M chlorotriethylsilane (69.13 ml, 69.13 mmol) in THF was added dropwise. The cooling bath was removed and the reaction solution was stirred for about another 2 hrs. Then it was cooled down to about −78° C. again, to which the same volume of n-butyllithium solution was injected, and it was stirred for about 1 hr and gradually warmed up to room temperature in about 40 min. Then it was cooled down to about −78° C. for about 20 min, to which a THF solution of 3-(3-chlorophenyl)-5-(4-chlorobenzoyl)indole (5.5 g, 15.027 mmol, see Preparation 8, below) was added and stirred for about 15 min at about −78° C. After the cooling bath was removed, the mixture was stirred for about 0.5 hr and 130 ml of ether was added. The mixture was stirred at about 57° C. under $N_2$ atmosphere overnight. TLC ($CH_2Cl_2$:MeOH 5/0.6, AcOEt:Hexane 1:1) showed the reaction was complete. It was cooled down to about 0 ° C. and 9 ml (75.14 mmol) of 4-morpholinecarbonyl chloride was injected and stirred for about 5 hrs. It was quenched by saturated $NH_4Cl$ (100 ml×3). The organic layer was stripped down, and the residue was taken into 250 ml $CH_2Cl_2$, which was washed with 2M HCl, (100 ml×2), saturated $NaHCO_3$ (100 ml×2) and brine (100 ml×3). The organic solution was dried over $Na_2SO$, and stripped down. The crude product was purified by silica gel flash chromatograph, eluting with a mixture solution of $CH_2Cl_2$ and methanol (5:0.25). The pure fractions were pooled and evaporated in vacuo to dryness. 7 g of the title compound was obtained (yield 83%). MS (Calc.): 561.2, MS (ES): 561.2.

EXAMPLE Z (±)-1-(4-Morpholinecarbamoyl)-3-(3-cholorophenyl)-5-[amino(4-chlorophenyl)(1-methyl-1H-imidazol-5-yl)methyl]indole:

The title compound was made analogously to the method described for making Example 4, using (±)-1-(4-morpholinecarbamoyl)-3-(3-chlorophenyl)-5-[(4-chlorophenyl)hydroxy(1-methyl-1H-imidazol-5-yl)methyl]indole (see Example Y) in place of (±)-1-methylsulfonyl-(3-chlorophenyl)-5-[(4-chlorophenyl)hydroxyl(1-methyl-1H-imidazol-5-yl) methyl]indole. Yield: 72%. MS (Calc.): 560.49, MS (ES): 560.30.

The following compounds can be synthesized analogously to the procedures detailed for Examples 1 to 4 but using the appropriate starting materials and modifications, which are well known to those of ordinary skill in the art. Examples 5, 6, 6, 18, 20, 22, B, D, F, J, L, N, P, R and X can be synthesized analogously to Example 4. Examples 9, 15, 17, 19, A, C, E, I, K, M, O, Q and W can be synthesized analogously to Example 2. Example U can be synthesized analogously to Example V.

Examples 13 and 14 were obtained by reacting the compound of Preparation 8, below, with iodomethane in the presence of $K_2CO_3$ in DMF at about 80° C. for about 5 hrs. The resulting intermediate (where Y is methyl, see table of Examples below) was divided into two lots. One lot was subjected to an synthetic scheme analogous to the first procedure described for Example 2 except the step of reacting it with methanesulfonyl chloride was not conducted, to obtain the compound of Example 13. The other lot of the intermediate was subjected to a synthetic scheme analogous to Example 4 to obtain the compound of Example 14.

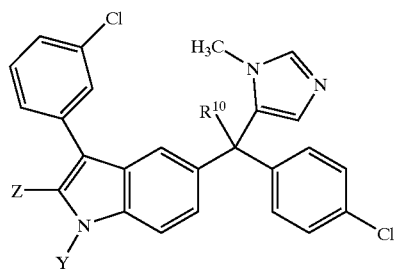

| Example No. | Z | Y | $R^{10}$ |
|---|---|---|---|
| 1 | H | H | OH |
| 2 | H | —S(O)₂—CH₃ | OH |
| 3 | H | —C(O)—N(CH₃)₂ | OH |
| 4 | H | —S(O)₂—CH₃ | NH₂ |
| 5 | H | H | NH₂ |
| 6 | H | —C(O)—N(CH₃)₂ | NH₂ |
| 7 | H | pyrrolidine-C(O)— | OH |
| 8 | H | pyrrolidine-C(O)— | NH₂ |
| 9 | H | —S(O)₂-Phenyl | OH |
| 10 | H | —S(O)₂-Phenyl | NH₂ |
| 11 | H | —C(O)—N(CH₂CH₃)₂ | OH |
| 12 | H | —C(O)—N(CH₂CH₃)₂ | NH₂ |
| 13 | H | —CH₃ | OH |
| 14 | H | —CH₃ | NH₂ |
| 15 | H | —S(O)₂—N(morpholine) | OH |
| 16 | H | —S(O)₂—N(morpholine) | NH₂ |
| 17 | H | —S(O)₂—N(4-methylpiperazine) | OH |
| 18 | H | —S(O)₂—N(4-methylpiperazine) | NH₂ |
| 19 | H | —S(O)₂—(4-aminophenyl) | OH |
| 20 | H | —S(O)₂—(4-aminophenyl) | NH₂ |
| 21 | H | —C(O)—CH₃ | OH |
| 22 | H | —C(O)—CH₃ | NH₂ |
| A | H | —S(O)₂—CF₃ | OH |
| B | H | —S(O)₂—CF₃ | NH₂ |
| C | H | —S(O)₂—CH₂—CF₃ | OH |

-continued

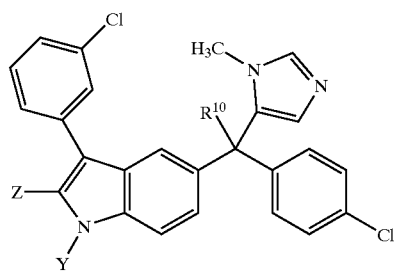

| Example No. | Z | Y | R¹⁰ |
|---|---|---|---|
| D | H | —S(O)₂—CH₂—CF₃ | NH₂ |
| E | H | ![piperazinone-mesyl] | OH |
| F | H | ![piperazinone-mesyl] | NH₂ |
| I | H | —C(O)—N(piperazine)NH | OH |
| J | H | —C(O)—N(piperazine)NH | NH₂ |
| K | H | —C(O)—N(piperazine)N—CH₂CH₂OH | OH |
| L | H | —C(O)—N(piperazine)N—CH₂CH₂OH | NH₂ |
| M | H | —C(O)—N(piperazine)N—CH₃ | OH |
| N | H | —C(O)—N(piperazine)N—CH₃ | NH₂ |
| O | H | —C(O)—NH₂ | OH |
| P | H | —C(O)—NH₂ | NH₂ |
| Q | H | —S(O)₂—(4-methylthiazol-2-yl-NHC(O)CH₃) | OH |

-continued (same structure as above)

| Example No. | Z | Y | R¹⁰ |
|---|---|---|---|
| R | H | —S(O)₂—(4-methylthiazol-2-yl-NHC(O)CH₃) | NH₂ |
| U | Cl | —C(O)-morpholine | NH₂ |
| V | Cl | —S(O)₂—CH₃ | NH₂ |
| W | H | —C(O)-(4-pyridyl) | OH |
| X | H | —C(O)-(4-pyridyl) | NH₂ |
| Y | H | —C(O)-morpholine | OH |
| Z | H | —C(O)-morpholine | NH₂ |

Preparation 1: 2-(3-Chlorophenyl)-N-methoxy-N-methyl-acetamide

A solution of 3-chlorophenylacetic acid (5.00 g, 29.3 mmol), 1-(3-dimethyl-aminopropyl)-3-ethylcarbodiimide HCL (6.18 g, 32.2 mmol), and 1-hydroxybenzotriazole (HOBt; 4.00 g, 29.3 mmol) in dichloromethane (DCM; 40 mL) was stirred at room temperature for about 10 minutes. The solution was cooled to about 0° C. To it were added N,O-dimethylhydroxylamine HCl (2.86 g, 29.0 mmol) and diisopropylethylamine (DIEA; 3.80 g, 29.3 mmol). The reaction mixture was warmed to room temperature and stirred for about 5 hours. The solution was diluted with 100 mL of DCM and washed with saturated NaHCO₃ aqueous solution (2 times), 1N HCl aqueous solution (2 times) and brine (2 times), dried over anhydrous MgSO₄, filtered and concentrated in vacuo. The liquid obtained was purified by column chromatography on silica eluting with EtOAc/hexane 1:1. The title compound was obtained as colorless liquid. Yield: 5.60 g, 89%. Rf=0.44 (silica, EtOAc/hexane 1:1). $^1$H NMR (300 MHz, CDCl₃) 7.18–7.34 (m, 4H), 3:76 (S, 2H), 3.66 (S, 3H), 3.22 (S, 3H).

Preparation 2: 2-(3-Chlorophenyl)-acetaldehyde

A suspension of LiAlH₄ (1.90 g, 51 mmol) in anhydrous ether (250 mL) was stirred at room temperature under nitrogen for about 1 hour. The suspension was cooled to about −45° C. To it was added drops of a solution of 2-(3-chlorophenyl)-N-methoxy-N-methyl-acetamide (8.19 g, 38.3 mmol, see Preparation 1) in 10 mL of anhydrous tetrahydrofuran (THF). The mixture was warmed to about 0° C. and stirred for about 3 hours. The solution was then cooled to about −45° C. To this solution was slowly added a solution of KHSO₄ (13 g) in water (about 30 mL) the resulting mixture was filtered through CELITE®. The filtrate was concentrated in vacuo, the resulting solution was diluted with DCM and washed with 1N HCl aqueous solution (2 times), and brine (2 times) dried over anhydrous MgSO₄, filtered and concentrated in vacuo. The title compound was obtained as a liquid (5.80 g), which was used immediately in the next step without further purification. Rf=0.71 (silica, EtOAc/hexane 1:3).

Preparation 3: 3-(3-Chlorophenyl)indole

A solution of 2-(3-chlorophenyl)-acetaldehyde (5.80 g, 37.5 mmol) and phenylhydrazine (6.22 g, 57.5 mmol) in glacial acetic acid (150 mL) was saturated with nitrogen by bubbling N₂ through the solution. The solution was then refluxed for about 2.5 hours. Solvent was removed in vacuo and the residue obtained was dissolved in DCM and washed with 1N HCl aqueous solution (2 times), saturated NaHCO₃ aqueous solution (2 times) and brine (2 times), dried over anhydrous MgSO₄, filtered and concentrated in vacuo. The crude product was purified by column chromatography on silica, eluting with EtOAc/hexane 1:6. The title compound was obtained as a reddish oil. Yield: 5.30 g, 62%. Rf=0.26 (silica, EtOAc/hexane 1:4)

Preparation 4: 3-(3-Chlorophenyl)-indoline 3-(3-Chlorophenyl)indole (5.30 g, 23.3 mmol) was dissolved in 50 mL of 1 M BH₃ in THF. The mixture was cooled to about 0° C. To the solution was added slowly TFA (50 mL). After addition, the solution was stirred for about 10 minutes. To the solution was added slowly 1M BH₃ in THF (40 mL). The mixture was stirred for about 5 minutes and then concentrated in vacuo. The residue was purified by column chromatography on silica, eluting with EtOAc/hexane 1:6. The title compound was obtained as an oil (Yield; 3.93 g, 74%). Rf=0.20 (Silica, EtOAc/hexane 1:4) MS (ES): 229.1; Calc. MW=229.7.)

Preparation 5: 1-Methylsulfonyl-3-(3-chlorophenyl) indoline

To a solution of 3-(3-chlorophenyl)indoline (3.88 g, 16.9 mmol) and DIEA (2.40 g, 18.6 mmol) in DCM (40 mL) was added dropwise methanesulfonyl chloride (2.13 g, 18.6 mmol) at about 0° C. The mixture was stirred for about 1.5 hours. The solution was diluted with DCM and washed with saturated NaHCO₃ solution (2 times), 1N HCl aqueous solution (2 times) and brine (2 times) and dried over anhydrous MgSO₄, filtered and concentrated in vacuo. The crude product was purified by column chromatography on silica, eluting with EtOAc/hexane 1:4. The title compound was obtained as an oil Yield: 4.40 g, 85%. Rf=0.41, silica, EtOAc/hexane 1:2. $^1$H NMR (300 MHz, CDCl₃) δ: 7.52 (d, 1H), 7.24–7.34 (m, 3H), 7.20 (s, 1H), 7.02–7.14 (m, 3H), 4.59 (t, 1H), 4.38 (t, 1H), 3.87 (dd, 1H), 2.92 (s, 3H).

Preparation 6: 1-Methylsulfonyl-3-(3-chlorophenyl)-5-(4-chlorobenzoyl)indoline

To a solution of 1-methylsulfonyl-3-(3-chlorophenyl) indoline (4.40 g, 14.3 mmol, see Preparation 5) and 4-chlorobenzoyl chloride (3.25 g, 18.6 mmol) in CS₂ (25 mL) was added portionwise AlCl₃ (7.62 g, 57.2 mmol) at about 0° C. A brown precipitate formed immediately. The mixture was stirred for about 2 hours. To the mixture was added slowly 100 mL of cold water containing 3 mL of concentrated HCl. The solution was diluted with DCM and the organic layer was separated and washed with 1N HCl aqueous solution (2 times), saturated NaHCO₃ aqueous solution (2 times) and brine (2 times), dried over anhydrous MgSO₄, filtered and concentrated in vacuo. The crude product was purified by column chromatography on silica, eluting with EtOAC/hexane 1:2. The title compound was obtained as a solid. Yield=3.90 g, 61%. Rf=0.24 (silica, EtOAc/hexane 1:2). MS (ES): 445.2; Calc. MW=445.4, $^1$H NMR (300 MHz, CDCl₃) δ: 7.67–7.76 (m, 3H), 7.53–7.59 (m, 2H), 7.48 (s, 1H), 7.44 (s, 1H), 7.30–7.32 (m, 2H), 7,20 (m, 1H), 7.09–7.14 (m, 1H), 4.65 (t, 1H), 4.50 (t, 1H), 3.98 (dd, 1H), 3.02 (s, 3H).

Preparation 7: 1-Methylsulfonyl-3-(3-chlorophenyl)-5-(4-chlorobenzoyl)indole

A solution of 1-methylsulfonyl-3-(3-chlorophenyl)-5-(4-chlorobenzoyl)indoline (350 mg) and 2,3-dichloro-5,6-dicyano-1,4-benzoquinone (356 mg) in dioxane (6 mL) was refluxed under N₂ for about 6 hours and then heated at about 95° C. overnight. The solvent was removed. The residue was purified by column chromatography on silica, eluting with EtOAc/hexane, 1:4. The title compound was obtained as a solid. MS(ES): 443.2, calc. Mw=443.4. Rf=0.38, silica, EtOAc/hexane, 1:2. 195 mg, yield: 56%.

Preparation 8: 3-(3-Chlorophenyl)-5-(4-chlorobenzoyl)indole

To a solution of 1-methylsulfonyl-3-(3-chlorophenyl)-5-(4-chlorobenzoyl)indole (11.44 g, 25.76 mmol, see Preparation 7) in anhydrous THF (150 ml) was added tetrabutylammonium fluoride (33.5 ml, 1.0 M solution in THF). The resulting solution was refluxed under nitrogen for about 3 hrs. The solvent was removed under reduced pressure. The residue was dissolved in EtOAc and washed with 1N HCl (2 times), saturated NaHCO₃ aqueous solution (2 times) and brine (2 times), dried over anhydrous MgSO₄, filtered and concentrated in vacuo. The residue was purified by column chromatography on silica, eluting with EtOAc/hexane 1:4. The title compound was obtained as a yellow solid. Yield= 8.1 g, 86%.

What is claimed is:

1. A method of treating a tumor, fibrosis, restenosis, neoplasm, fungal infection, arteriosclerosis, carcinoma, benign tumor, retina disease, hepatitis, renal disease, myeloid leukemia, viral infection, nervous system tumor, viral infection, breast tumor, pancreas tumor, or brain tumor in a subject in need thereof, which comprises administering to said subject an effective amount of a compound of formula (I):

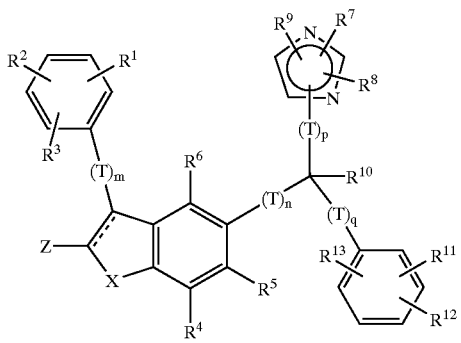

(I)

or a pharmaceutically acceptable salt thereof, wherein

──────── represents an optional bond;

m, n, p, and q are each independently 0 or 1;

T for each occurrence is independently selected from the group consisting of $CR^{26}R^{27}$, S, O, C(O), S(O)$_2$ and $NR^{28}$;

X is N—Y, O or S where Y is selected from the group consisting of H, $CR^{14}R^{15}R^{16}$, $S(O)R^{17}$, $S(O)_2R^{18}$, $C(O)R^{19}$, $C(O)NR^{20}R^{21}$, $C(S)NR^{22}R^{23}$, $C(O)OR^{24}$, $C(S)OR^{25}$, $S(O)NR^{29}R^{30}$, and $S(O)_2NR^{31}R^{32}$;

Z is selected from the group consisting of H, cyano, halo, $CR^{14}R^{15}R^{16}$, $S(O)R^{17}$, $S(O)_2R^{18}$ and $C(O)R^{19}$;

$R^1$, $R^2$, $R^3$, $R^4$, $R^5$, $R^6$, $R^{11}$, $R^{12}$, $R^{13}$, $R^{14}$, $R^{15}$, $R^{16}$, $R^{26}$ and $R^{27}$ are each independently selected from the group consisting of H, halo, hydroxy, thio, and cyano, or an optionally substituted moiety selected from the group consisting of alkyl, akenyl, alkynyl, cycloalkyl, cycloalkyl-alkyl, aryl, arylalkyl, alkyloxy, aryloxy, alkylthio, arylthio, alkylamino, arylamino and alkyl carbonyl amino;

or $R^1$ and $R^2$ when on adjacent positions, or $R^4$ and $R^5$, or $R^{11}$ and $R^{12}$, are taken together to form a bivalent radical selected from the group consisting of —O—CH$_2$—O—, —O—CH$_2$—CH$_2$—O—, —O—CH=CH—, —OCH$_2$—CH$_2$—, —O—CH$_2$—CH$_2$—CH$_2$— and —CR$^{33}$=CR$^{34}$—CR$^{35}$=CR$^{36}$—;

$R^7$, $R^8$, and $R^9$ are each independently selected from the group consisting of H, halo, aryl, alkyl, substituted alkyl, alkyloxy, alkylthio, aryloxy, arylthio amino, mono- or di-alkylamino, hydroxycarbonyl, alkoxycarbonyl, alkyl-S(O)-alkyl, alkyl-S(O)$_2$-alkyl, cyanoarylalkyl, arylalkyl and substituted arylalkyl;

$R^{10}$ is selected from the group consisting of H, amino, azido, hydroxy, halo, alkyl, substituted alkyl, cyano, hydroxyalkyl, hydroxycarbonyl, aminoalkyl, mono- or di-alkylaminoalkyl, mono- or di-alkylamino, alkoxy, alkylcarbonylalkyl, cyanoalkyl, alkyloxycarbonylalkyl, carboxyalkyl, cycloalkyl, cycloalkylamino, cycloalkylhydroxy, imidazoyl, substituted imidazoyl, aminocarbonylalkyl, aryloxy, thio, alkylthio, $OS(O_2)R^{18}$, $OC(O)R^{19}$, $OC(O)NR^{20}R^{21}$, $OC(S)NR^{22}R^{23}$, $OS(O)NR^{29}R^{30}$, $OS(O)_2NR^{31}R^{32}$ and aryl thio;

and $R^{17}$, $R^{18}$, $R^{19}$, $R^{20}$, $R^{21}$, $R^{22}$, $R^{23}$, $R^{24}$, $R^{25}$, $R^{28}$, $R^{29}$, $R^{30}$, $R^{31}$, $R^{32}$ and $R^{37}$ for each occurrence are each independently selected from the group consisting of H, alkyl, substituted alkyl, alkenyl, cycloalkyl, aryl and arylalkyl;

or $R^{20}$ and $R^{21}$, or $R^{22}$ and $R^{23}$, or $R^{29}$ and $R^{30}$, or $R^{31}$ and $R^{32}$ are taken together to form a bivalent radical selected from the group consisting of —(CH$_2$)$_r$—NR$^{37}$—(CH$_2$)$_s$—, —(CH$_2$)$_r$—O—(CH$_2$)$_s$— and —(CR$^{38}$R$^{39}$)$_t$—, where r and s are each independently 1 to 3 and t is 2 to 6;

$R^{33}$, $R^{34}$, $R^{35}$, $R^{36}$, $R^{38}$ and $R^{39}$ are each independently selected from the group consisting of H, halo, cyano, alkyl, substituted alkyl aryl, substituted aryl, alkyloxy, aryloxy, alkylthio, arylthio, alkylamino, arylamino, hydroxy and thio.

2. A method of treating a tumor, fibrosis, restenosis, neoplasm, fungal infection, arteriosclerosis, carcinoma, benign tumor, retina disease, hepatitis, renal disease, myeloid leukemia, viral infection, nervous system tumor, viral infection, breast tumor, pancreas tumor, or brain tumor in a subject in need thereof, which comprises administering to said subject an effective amount of a compound of formula (II):

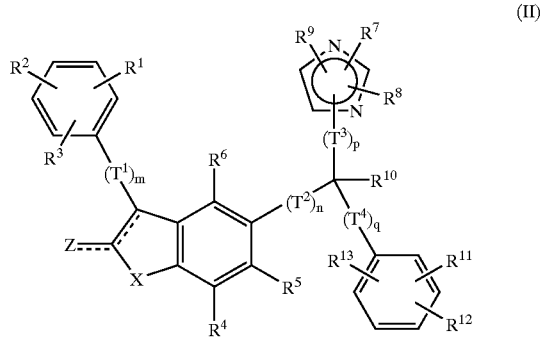

(II)

or a pharmaceutically acceptable salt thereof, wherein

──────── represents an optional bond, provided that only one of the optional bonds is present in a compound of formula (I);

m, n, p, and q are each independently 0, 1, or 2;

$T^1$, $T^2$, $T^3$ and $T^4$ for each occurrence are each independently selected from the group consisting of $CR^{26}R^{27}$, S, O, C(O), S(O)$_2$ and $NR^{28}$;

X is N—Y, O or S where Y is selected from the group consisting of H, $CR^{14}R^{15}R^{16}$, $S(O)R^{17}$, $S(O)_2R^{18}$, $C(O)R^{19}$, $C(O)NR^{20}R^{21}$, $C(S)NR^{22}R^{23}$, $C(O)OR^{24}$, $C(S)OR^{25}$, $S(O)NR^{29}R^{30}$ and $S(O)_2NR^{31}R^{32}$;

Z is selected from the group consisting of H, hydroxy, alkoxy, aryloxy, cyano, halo, $CR^{14}R^{15}R^{16}$, $S(O)R^{17}$, $S(O)_2R^{18}$, $C(O)R^{19}$, $C(O)NR^{20}R^{21}$, $C(O)OR^{24}$, $C(S)NR^{22}R^{23}$, $C(S)OR^{25}$, $S(O)NR^{29}R^{30}$ and $S(O)_2NR^{31}R^{32}$, provided that when the optional bond connected to Z is present then Z is oxygen or sulfur;

$R^1$, $R^2$, $R^3$, $R^4$, $R^5$, $R^6$, $R^{11}$, $R^{12}$, $R^{13}$, $R^{14}$, $R^{15}$, $R^{16}$, $R^{26}$ and $R^{27}$ for each occurence are each independently selected from the group consisting of H, halo, hydroxy, thio, and cyano, or an optionally substituted moiety selected from the group consisting of alkyl, akenyl, alkynyl, cycloalkyl, cycloalkyl-alkyl, aryl, arylalkyl, alkyloxy, aryloxy, alkylthio, arylthio, alkylamino, arylamino and alkyl carbonyl amino;

or each pair of $R^1$ and $R^2$, $R^4$ and $R^5$, and $R^{11}$ and $R^{12}$, when on adjacent positions, is independently taken together to form a bivalent radical selected from the group consisting of —O—CH$_2$—O—, —O—CH$_2$—CH$_2$—O—, —O—CH=CH—, —O—CH$_2$—CH$_2$—, —O—CH$_2$—CH$_2$—CH$_2$— and —CR$^{33}$=CR$^{34}$—CR$^{35}$=CR$^{36}$—;

R$^7$, R$^8$, and R$^9$ are each independently H, halo, amino, cyano, hydroxycarbonyl, or an optionally substituted moiety selected from the group consisting of aryl, alkyl, alkyloxy, alkylthio, aryloxy, arylthio, alkoxycarbonyl, alkyl-S(O)-alkyl, alkyl-S(O)$_2$-alkyl, cyanoarylalkyl, and arylalkyl, provided that when R$^7$, R$^8$, or R$^9$ is bound to one of the nitrogen atoms of the imidazolyl ring, R$^7$, R$^8$, or R$^9$ is H or an optionally substituted moiety selected from the group consisting of aryl, alkyl, alkoxycarbonyl, alkyl-S(O)-alkyl, alkyl-S(O)$_2$-alkyl, cyanoarylalkyl, and arylalkyl;

R$^{10}$ is selected from the group consisting of H, amino, azido, hydroxy, halo, alkyl, substituted alkyl, cyano, hydroxycarbonyl, mono- or di-alkylamino, alkyloxy, cycloallyl, cycloalkylamino, cycloalkyloxy, imidazolyl, substituted imidazolyl, aryloxy, thio, alkylthio, arylthio, OS(O$_2$)R$^{18}$, OC(O)R$^{19}$, OC(O)NR$^{20}$R$^{21}$, OC(S)NR$^{22}$R$^{23}$, OS(O)NR$^{29}$R$^{30}$ and OS(O)$_2$NR$^{31}$R$^{32}$;

R$^{17}$ and R$^{18}$, for each occurrence are each independently H, OH or an optionally substituted moiety selected from the group consisting of alkyl, alkenyl, cycloalkyl, aryl, arylalkyl and heterocyclyl;

R$^{19}$, R$^{20}$, R$^{21}$, R$^{22}$, R$^{23}$, R$^{24}$, R$^{25}$, R$^{28}$, R$^{29}$, R$^{30}$, R$^{31}$, and R$^{32}$ for each occurrence are each independently H or an optionally substituted moiety selected from the group consisting of alkyl, alkenyl, cycloalkyl, aryl, arylalkyl and heterocyclyl;

or each pair of R$^{20}$ and R$^{21}$, or R$^{22}$ and R$^{23}$, or R$^{29}$ and R$^{30}$, and R$^{31}$ and R$^{32}$ is independently taken together to form a bivalent radical selected from the group consisting of —(CH$_2$)$_r$—NR$^{40}$—(CH$_2$)$_s$—, —(CH$_2$)$_r$—O—(CH$_2$)$_s$—, —(CR$^{38}$R$^{39}$)$_t$—, and —(CH$_2$)$_r$—NR$^{40}$—(C(O))$_u$— where r and s are each independently 1 to 3, t is 2 to 6 and u is 1 or 2;

R$^{33}$, R$^{34}$, R$^{35}$, R$^{36}$, R$^{38}$ and R$^{39}$ for each occurrence are each independently selected the group consisting of H, amino, halo, cyano, alkyl, substituted alkyl aryl, substituted aryl, alkyloxy, aryloxy, alkylthio, arylthio, mono- or di-alkylamino, arylamino, hydroxy, heterocyclyl and thio;

and R$^{40}$ is H, S(O)$_2$R$^{18}$, C(O)R$^{19}$, C(O)NR$^{20}$R$^{21}$, C(S)NR$^{22}$R$^{23}$, C(O)OR$^{24}$, C(S)OR$^{25}$, and S(O)$_2$NR$^{31}$R$^{32}$, or an optionally substituted moiety selected from the group consisting of alkyl, alkenyl, cycloalkyl, aryl, arylalkyl and heterocyclyl.

\* \* \* \* \*

UNITED STATES PATENT AND TRADEMARK OFFICE
CERTIFICATE OF CORRECTION

PATENT NO.    : 6,509,336 B1                                            Page 1 of 1
DATED         : January 21, 2003
INVENTOR(S)   : Xin Zheng Dong and Yeelana Shen It is certified that error appears in the above-identified patent and that said Letters Patent is hereby corrected as shown below:

Column 43,
Line 22, delete "_____" and insert -- _____ --

Column 44,
Line 37, delete "_____" and insert -- _____ --
Line 39, delete "(I)" and insert -- (II) --

Column 45,
Line 17, delete "cyclallyl" and insert -- cycloalkyl --

Column 46,
Line 15, insert -- , -- between "alkyl" and "aryl"

Signed and Sealed this

Eleventh Day of May, 2004

JON W. DUDAS
*Acting Director of the United States Patent and Trademark Office*